US010076637B2

(12) United States Patent
Tegg

(10) Patent No.: US 10,076,637 B2
(45) Date of Patent: Sep. 18, 2018

(54) CATHETER DEFLECTION ACTUATOR PROVIDING MECHANICAL ADVANTAGE

(71) Applicant: St. Jude Medical, Cardiology Division, Inc., St. Paul, MN (US)

(72) Inventor: Troy T. Tegg, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 652 days.

(21) Appl. No.: 14/592,309

(22) Filed: Jan. 8, 2015

(65) Prior Publication Data

US 2015/0196736 A1    Jul. 16, 2015

Related U.S. Application Data

(60) Provisional application No. 61/926,814, filed on Jan. 13, 2014.

(51) Int. Cl.
*A61M 25/01* (2006.01)
*A61B 18/00* (2006.01)

(52) U.S. Cl.
CPC .  *A61M 25/0136* (2013.01); *A61B 2018/0091* (2013.01); *A61M 25/0147* (2013.01); *A61M 2025/015* (2013.01)

(58) Field of Classification Search
CPC .. A61B 2017/00323; A61B 2017/3468; A61B 2017/347; A61B 2017/00318;

(Continued)

(56) References Cited

U.S. PATENT DOCUMENTS

2004/0127847 A1*  7/2004  DuBois ............. A61M 25/0147
                                                  604/95.04
2007/0078455 A1*  4/2007  Rashidi ............. A61B 18/1492
                                                  606/41

(Continued)

FOREIGN PATENT DOCUMENTS

WO        2013150871        10/2013

OTHER PUBLICATIONS

Partial International Search Report for PCT Application No. PCT/US2015/010587, dated May 11, 2015. 1 pg.

*Primary Examiner* — Emily Schmidt
*Assistant Examiner* — Alexandra Lalonde
(74) *Attorney, Agent, or Firm* — Dykema Gossett PLLC

(57) ABSTRACT

Deflection actuators configured to provide variable mechanical advantage and to optionally maintain a desired state of deflection are disclosed. Each deflection actuator may comprise a plurality of planar components, at least one of which is adapted to move relative to at least one other component. The planar components may comprise a channeled platform and a pivotable base mounted adjacent to the channeled platform. The platform may comprise a slider trough to slidably retain a slider. The base may have a cam arm pivotally connected to it and adapted to push a slider in its trough, whereby pivoting of the pivotable base relative to the channeled platform produces linear motion by the slider in its slider trough. The deflection actuator may also comprise a friction-lock knob, a knob receiver, and a pivot hub to selectably produce friction between various components to hold a catheter shaft in a desired state of deflection.

30 Claims, 18 Drawing Sheets

(58) Field of Classification Search
CPC .......... A61B 2017/00327; A61B 2017/00464; A61B 1/0052; A61B 2018/0091; A61M 2025/015; A61M 25/0147; A61M 25/0136; A61M 25/0133
See application file for complete search history.

(56) References Cited

U.S. PATENT DOCUMENTS

| | | | |
|---|---|---|---|
| 2010/0069834 A1* | 3/2010 | Schultz | A61M 25/0136 604/95.04 |
| 2011/0282176 A1 | 11/2011 | Tegg | |
| 2013/0204096 A1 | 8/2013 | Ku | |
| 2013/0324973 A1* | 12/2013 | Reed | A61M 25/0136 604/528 |
| 2014/0066716 A1 | 3/2014 | Arai et al. | |
| 2015/0057610 A1* | 2/2015 | Osypka | A61B 17/3468 604/95.04 |

* cited by examiner

CATHETER DEFLECTION ACTUATOR PROVIDING MECHANICAL ADVANTAGE

CROSS-REFERENCE TO RELATED APPLICATIONS

This application claims the benefit of U.S. provisional application No. 61/926,814, filed 13 Jan. 2014, which is hereby incorporated by reference as though fully set forth herein.

BACKGROUND a. Field

The instant disclosure relates to handles and actuators for steerable medical devices. In one particular form, this disclosure relates to a catheter actuator that includes one or more cam arms that provide mechanical advantage when tensioning one or more tension members.

b. Background Art

Electrophysiology catheters are used in a variety of diagnostic, therapeutic, and/or mapping and ablative procedures to diagnose and/or correct conditions such as atrial arrhythmias, including, for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death.

Typically, a catheter is deployed and manipulated through a patient's vasculature to the intended site, for example, a site within the patient's heart. The catheter typically carries one or more electrodes that can be used for cardiac mapping or diagnosis, ablation, and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. These lesions disrupt undesirable cardiac activation pathways and thereby limit, corral, or prevent errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to selectively position the distal portion of the catheter during an electrophysiological procedure. The proximal end of the catheter can be manipulated to guide the catheter through a patient's vasculature. The distal tip can be deflected by a tension member attached at the distal end of the catheter and extending proximally to an actuator in a control handle that controls the application of tension on the tension member.

The foregoing discussion is intended only to illustrate the present field and should not be taken as a disavowal of claim scope.

BRIEF SUMMARY OF THE DISCLOSURE

In one embodiment, a deflection actuator comprises (i) a channeled platform adapted to be fixedly mounted to a catheter handle housing, wherein the channeled platform comprises a first slider trough; (ii) a pivotable base mounted adjacent to the channeled platform and adapted to pivot relative to the channeled platform; (iii) a first slider slidably mounted in the first slider trough; and (iv) a first cam arm pivotally connected to the pivotable base and adapted to push the first slider in the first slider trough, whereby pivotable motion of the pivotable base relative to the channeled platform produces linear motion by the first slider in the first slider trough. The deflection actuator may further comprise a pivot hub rotatably mounted in a hole through the channeled platform, wherein the pivot hub comprises a first keyed section keyed to the pivotable base such that the pivot hub and the pivotable base rotate together.

In another embodiment, a deflection actuator comprises the following: (a) a pivot hub comprising an end surface, an upper keyed surface, an intermediate bearing surface, a lower keyed surface, and a screw-member-receiving hole oriented along a pivot hub longitudinal axis; (b) a cover disk comprising a cover disk central hole mounted on the upper keyed surface of the pivot hub, whereby the pivot hub is adapted to rotate with the cover disk; (c) a pivotable base comprising a pivotable base central hole mounted on the lower keyed surface of the pivot hub, whereby the pivot hub is adapted to rotate with the pivotable base; (d) a channeled platform adapted to be fixedly mounted to a catheter handle housing, the channeled platform comprising (i) a first slider trough and (ii) a channeled platform central hole pivotably mounted on the intermediate bearing surface of the pivot hub, whereby the pivot hub is adapted to freely rotate in the channeled platform central hole; (e) a knob receiver mounted above the end surface of the pivot hub; (f) a friction-lock knob mounted on the knob receiver; (g) a first slider comprising a proximal end and a distal end, the first slider slidably mounted in the first slider trough; and (h) a first cam arm comprising a proximal end and a distal end, wherein the distal end of the first cam arm is pivotally connected to the pivotable base, wherein the proximal end of the first cam arm is adapted to push the distal end of the first slider in the first slider trough, whereby pivotable motion of the pivotable base relative to the channeled platform produces linear movement of the first slider in the first slider trough. The embodiment may include multiple cam arm and multiple sliders, and a tension member anchor may be mounted to each of the sliders.

In yet another embodiment, a catheter handle comprises a deflection actuator pivotably mounted in a handle housing. The deflection actuator may comprise (a) a channeled platform fixedly mounted in the handle housing, the channeled platform comprising a first planar surface, a second planar surface, a first slider trough, and a second slider trough; (b) a pivotable base rotatably mounted in the handle housing against the first planar surface of the channeled platform, wherein the pivotable base is adapted to pivot relative to the channeled platform; (c) a cover disk rotatably mounted in the handle housing against the second planar surface of the channeled platform; (d) a pivot hub extending through the cover disk, the channeled platform, and the pivotable base; (e) a knob receiver comprising a threaded member mounted along a longitudinally-extending knob receiver pivot axis, wherein the threaded member is also threaded into a blind hole extending along a longitudinally-extending pivot hub pivot axis; (f) a friction-lock knob fixedly mounted to the knob receiver to rotate therewith; and (g) a first thumb boss, a second thumb boss, and a crossmember extending between and connecting the two thumb bosses, wherein the crossmember is affixed to the pivotable base. Further, the pivot hub, in one embodiment, may comprise (i) a first keyed surface keyed to a hole through the pivotable base; (ii) a second keyed surface keyed to a hole through the cover disk; and (iii) a bearing surface mounted in a hole through the channeled platform; (iv). The catheter handle may further comprise a first slider slidably mounted in the first slider trough, a second slider slidably mounted in the second slider trough; a first cam arm pivotally connected to the pivotable base and adapted to push the first slider in the first slider trough, whereby pivotable motion of the pivotable base relative to the channeled platform produces linear movement of the first slider in the first slider trough; and a second cam arm pivotally connected to the pivotable base and adapted to push the second slider in the second slider trough, whereby pivotable motion of the pivotable base relative to the channeled platform produces linear movement of the second slider in the second slider trough.

The above summary of the present disclosure is not intended to describe each disclosed embodiment or every implementation of the present disclosure. The foregoing and other aspects, features, details, utilities, and advantages of the present disclosure will be apparent from reading the following description and claims, and from reviewing the accompanying drawings. The description that follows more particularly exemplifies one or more illustrative embodiments. In several places throughout this disclosure, guidance is provided through examples, which can be used in various combinations. The recited examples are representative and should not be interpreted as exclusive or exhaustive.

DETAILED DESCRIPTION OF EMBODIMENTS

Figure 1:
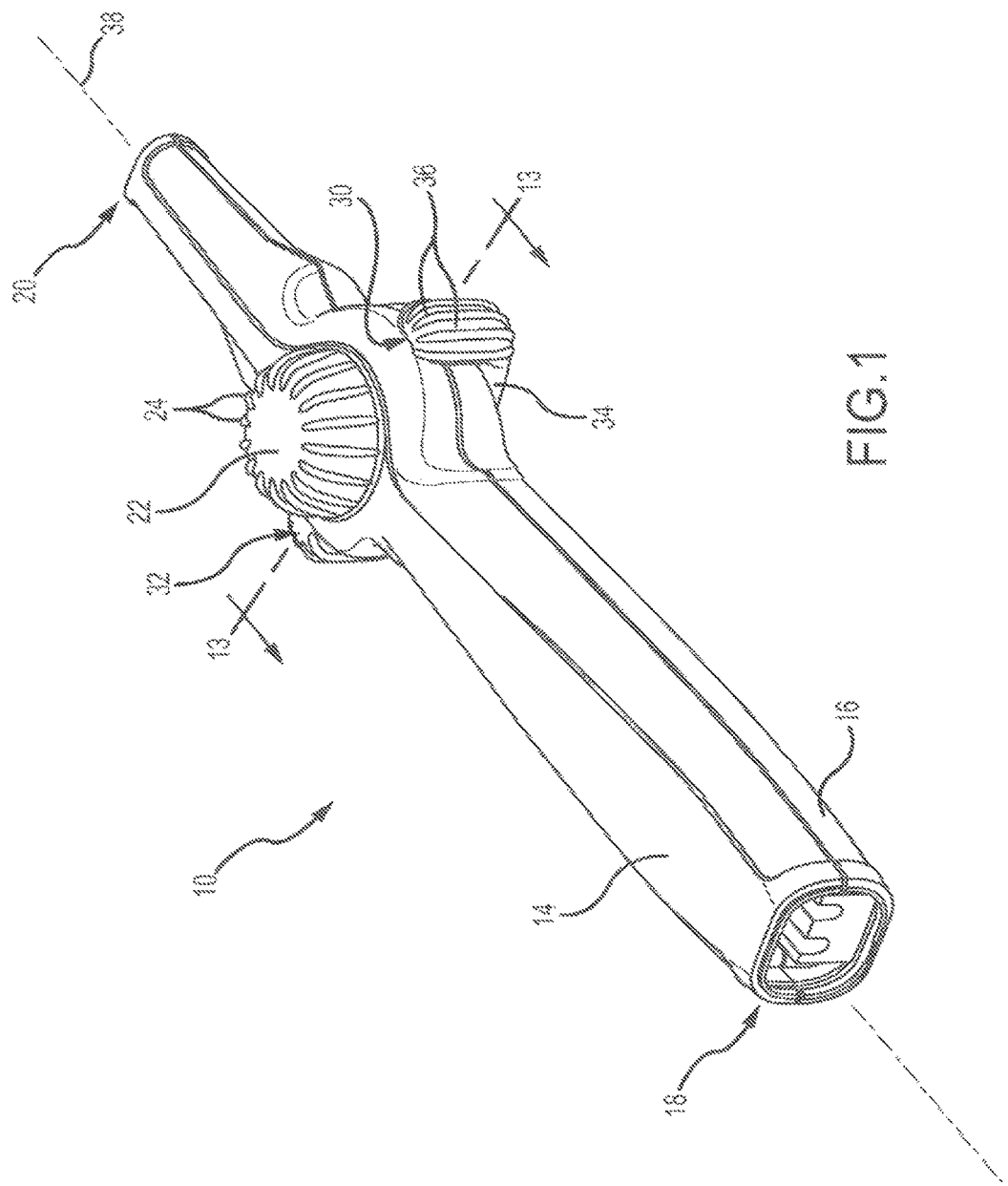
FIG. 1 is an isometric view of the top and right or starboard side of a catheter handle having a deflection actuator according to one embodiment of the present disclosure, with various parts of the catheter removed for clarity.

FIG. 1 is an isometric view of a catheter handle 10 that includes a pivotable deflection actuator 12 (shown to better advantage in FIG. 2) according to an embodiment of the present invention. For simplicity, FIG. 1 does not depict a full catheter, which would include a catheter shaft, electrical connections, and other components that are not shown in this figure. In this embodiment, the catheter handle 10 comprises an upper handle housing 14 and a lower handle housing 16, each of which extends from a proximal end 18 of the catheter handle 10 to a distal end 20 of the catheter handle 10. A friction-lock knob 22 comprising a plurality of knob knurls 24 is rotatably mounted above the upper handle housing 14. As will be discussed further below, the friction-lock knob, in this embodiment, includes a pair of knob limit pins 26, 28 (shown in, for example, FIGS. 11 and 15) that extend into or through arcuate slots (not shown, but discussed further below with regard to FIG. 11) through the upper handle housing 14 in order to limit how far a user may rotate the friction-lock knob 22 clockwise or counterclockwise.

The deflection actuator 12 also includes a first thumb boss 30, a second thumb boss 32, and a crossmember 34 extending between and connecting the two thumb bosses. Each thumb boss may include a plurality of grooves or a plurality of raised ridges or knob knurls 36, as shown in FIG. 1, to facilitate positive interaction between a user's hands and the bosses. In FIG. 1, the deflection actuator 12 is shown in a neutral or nearly neutral orientation, where the first and second thumb bosses symmetrically straddle a longitudinal axis 38 of the catheter handle 10.

Figure 2:
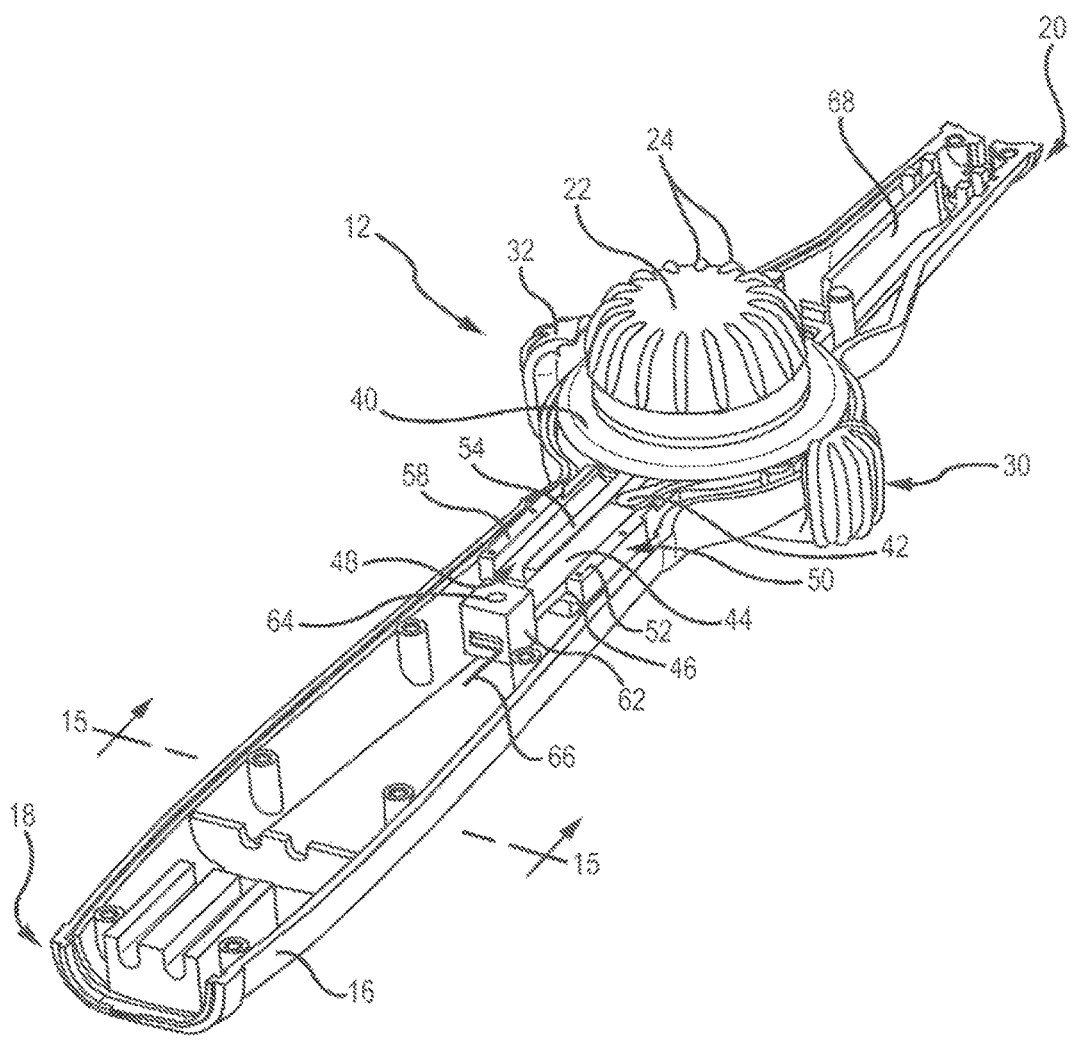
FIG. 2 is an isometric view of the catheter handle depicted in FIG. 1, with the upper handle housing and select other components removed to reveal the deflection actuator in a slightly-actuated configuration.

FIG. 2 is similar to FIG. 1 and is an isometric view of the deflection actuator 12 mounted in the lower handle housing 16. In this figure, the upper handle housing 14 has been removed to reveal a number of components of the deflection actuator 12. For example, the actuator according to this embodiment may include a cover disk 40 that may be located under the upper handle housing 14 in the fully-assembled handle. A first cam arm 42 may be seen in FIG. 2. In particular, the first cam arm 42 is shown with its proximal end (also known as an arcuate pushing end 108, which is labeled in FIG. 6) pressing against a distal end (also known as a slider pushed end 110, which is labeled in FIG. 6) of a first slider 44 that is longitudinally slidably mounted in a first slider trough or slider guide channel 46. The first slider trough and a second slider trough 48 are formed in a channeled platform 50 comprising part of the deflection actuator 12. For instance, the first slider trough 46 is formed by a starboard wall 52, a central wall 54, and a lower wall 56. Similarly, the second slider trough 48 is formed by a port wall 58, the central wall 54, and the lower wall 56. In FIG. 2, no second slider is present, but a second slider 60 is shown in, for example, FIGS. 5 and 6 (a second slider may be present if bidirectional deflection is desired).

A first tension member clamp or anchor 62 is shown affixed to a proximal end of the first slider 44. The first tension member anchor includes a screw hole 64 to accommodate a screw or other fixation member (not shown). As will be described further below, when a screw is tightened in the screw hole 64, the first tension member anchor 62 pinches or traps a first tension member (or pullwire or puller wire) 66 against a portion of the first slider 44 (see also FIG. 15). Then, when the deflection actuator 12 is actuated to move the first slider 44, the first slider also simultaneously moves or pulls the first tension member 66. Each tension member may be metallic (e.g., stainless steel) or non-metallic (e.g., Kevlar or some other natural or manmade material). It is also possible to see a tension member separation wall 68 in FIG. 2. In this embodiment, the tension member separation wall 68 comprises part of the lower handle housing 16.

Figure 3:
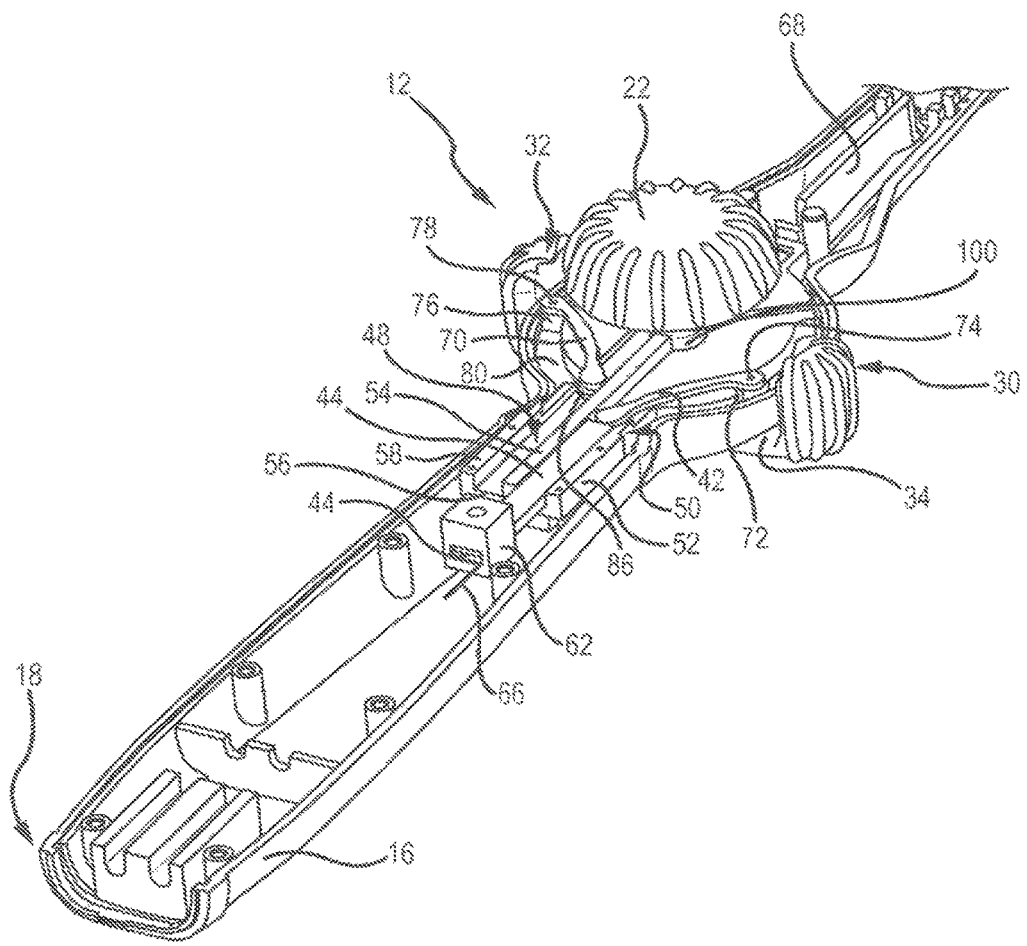
FIG. 3 is a fragmentary, isometric view of the catheter handle depicted in FIGS. 1 and 2, with the deflection actuator in the same, slightly-actuated configuration shown in FIGS. 1 and 2, but with additional components removed to reveal certain additional aspects of the deflection actuator.

FIG. 3 is a view similar to FIG. 2, but with the cover disk 40 removed to reveal a second cam arm 70. With the cover disk removed, it is also possible to see that the distal end of the first cam arm is pivotably mounted to a first pin block 72 by a first pivot pin 74. Similarly, a distal end of the second cam arm 70 is pivotably attached to a second pin block 76 by a second pivot pin 78. The first pin block 72 is attached to (or comprises an integral part of) a pivotable base 80 that rotates relative to the channeled platform 50. In particular, the first pin block 72 rides in a first pin block channel 82 (labeled in FIG. 4) formed in the channeled platform 50, and the second pin block 72 rides in a second pin block channel 82 (labeled in FIG. 4) that is also formed in the channeled platform 50. As will be discussed further below, the proximal end of each cam arm 42, 70 may have a roller 86 rotatably mounted to it. In FIG. 3, a second roller 86 is visible. These rollers 86 which may be present on the proximal ends of the cam arms are described further below while discussing figures in which these rollers are more clearly visible (see, for example, a discussion of FIGS. 8, 10, and 16).

Figure 4:
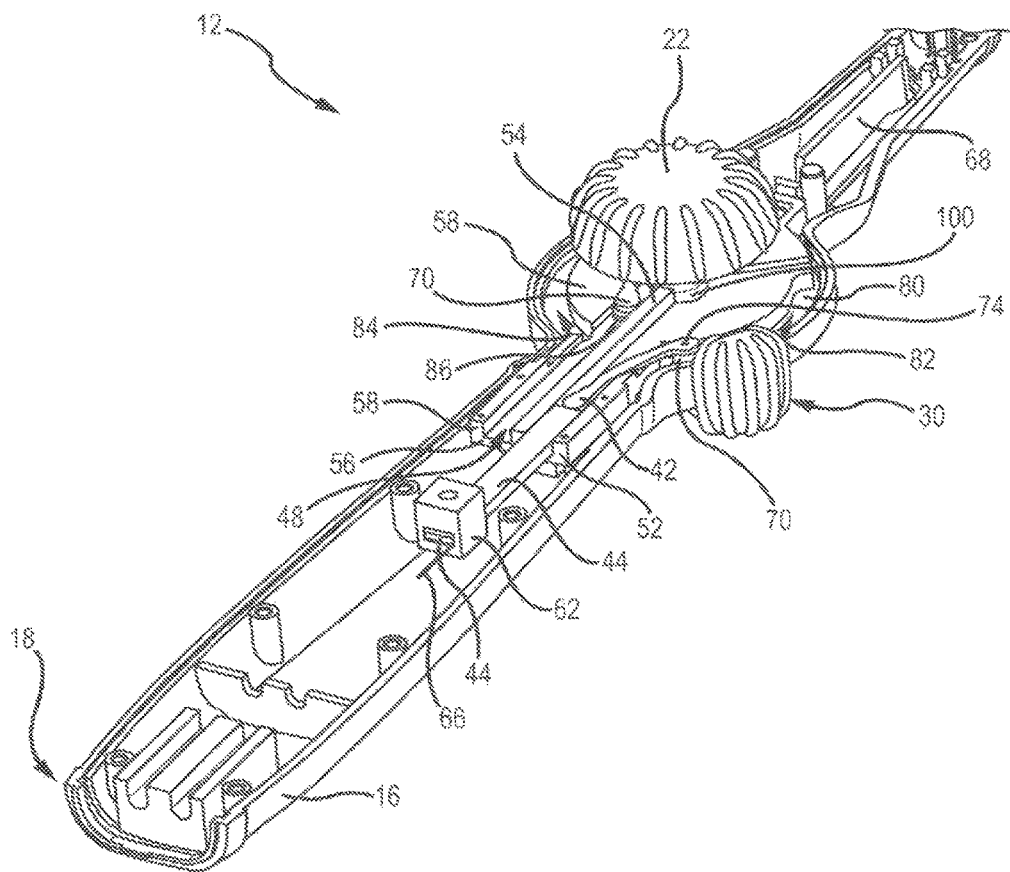
FIG. 4 is similar to FIG. 3, but depicts the deflection actuator in a near-fully-actuated configuration.

FIG. 4 is similar to FIG. 3, but shows the deflection actuator 12 in a more fully deflected configuration. In particular, comparing FIG. 4 to FIG. 3, it is possible to see that the first thumb boss 30 is in a more proximal position in FIG. 4 than it is in FIG. 3 (the deflection actuator has been rotated slightly clockwise in FIG. 4 relative to its position in FIG. 3). This in turn causes the first cam arm 42 to be shifted proximally compared to its position in FIG. 3, which would pull the first tension member 66 closer to the proximal end 18 of the lower handle housing 16.

Figure 5:
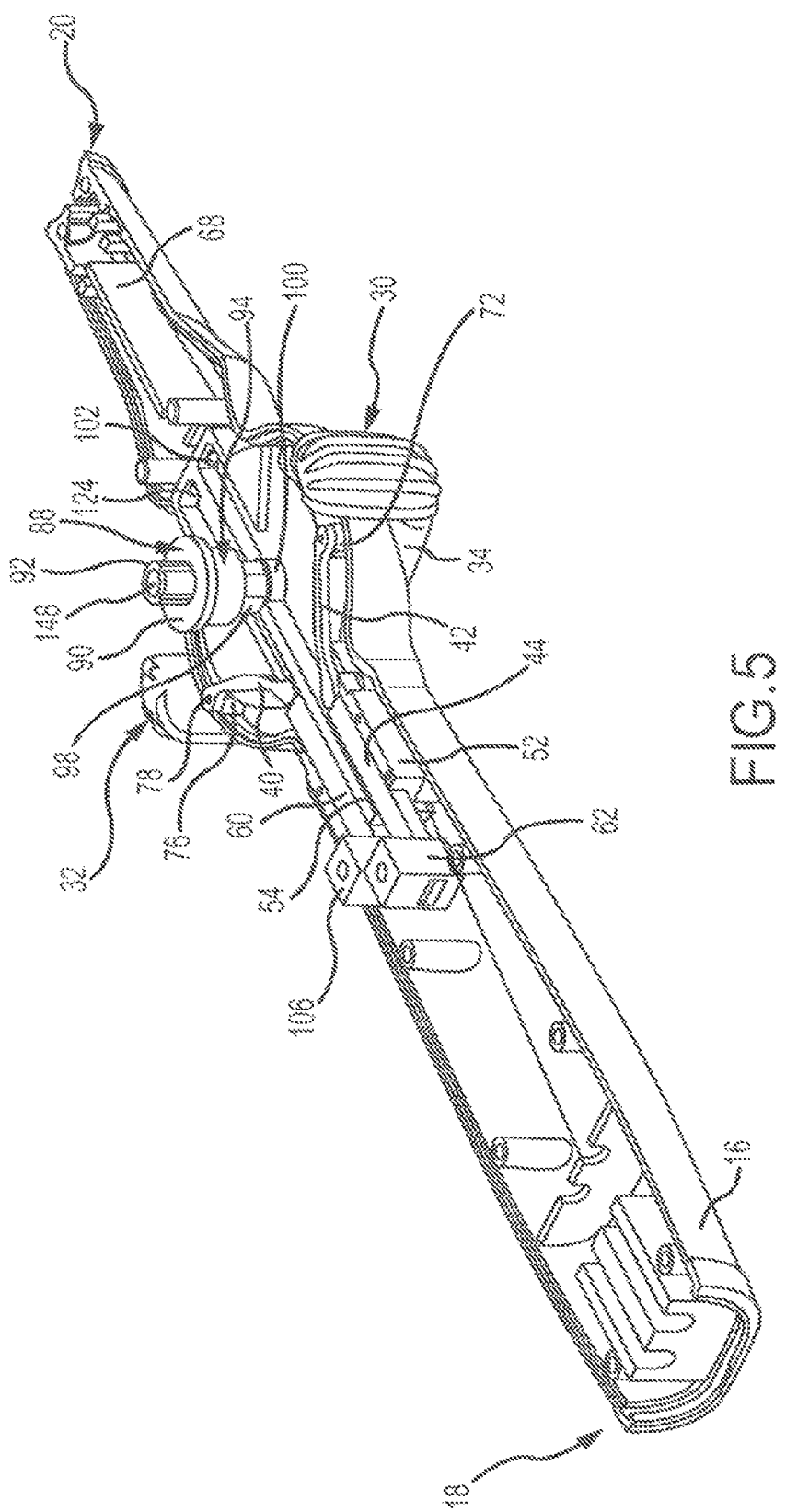
FIG. 5 is most similar to FIG. 3, but shows the friction-lock knob removed, and both sliders and tension member anchors in place.
Figure 12:
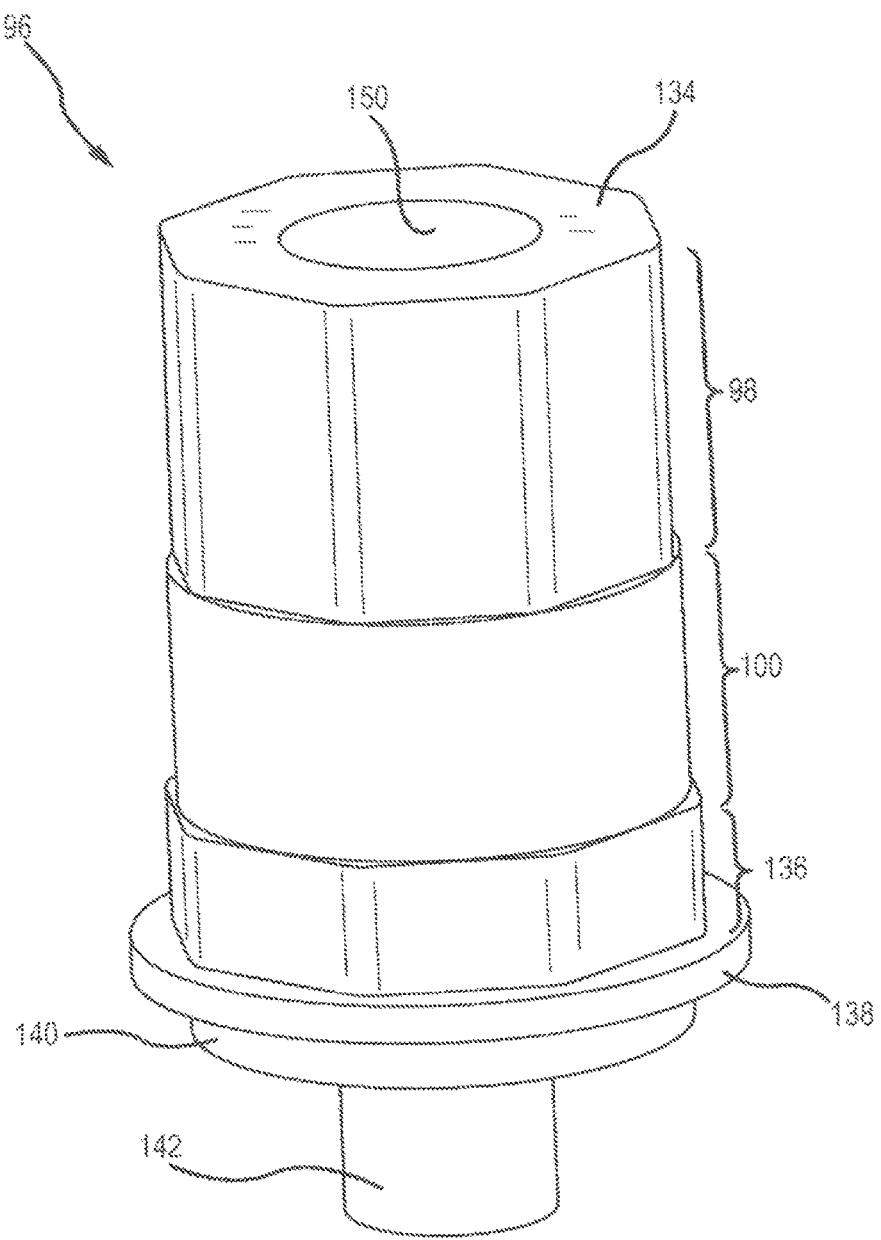
FIG. 12 is an enlarged, fragmentary view of a pivot hub.

In FIG. 5, the deflection actuator 12 has returned to a near-neutral configuration, similar to what is shown in FIG. 3. In FIG. 5, however, the friction-lock knob 22 has been removed, revealing a knob receiver 88. The knob receiver comprises a knob support ring 90 and a splined, knob-mounting shaft 92. The knob support ring is mounted above a lower body 94 of the knob receiver 88. In this figure, it is also possible to see slightly more of a pivot hub 96 on which the knob receiver 88 is mounted. In particular, in FIG. 5, it is possible to see a upper keyed section 98 and an intermediate bearing surface 100, both comprising part of the pivot hub 96. FIG. 12 is an isometric and enlarged view of this pivot hub 96, which will be described further below in connection with the discussion of FIG. 12. Referring back to FIG. 5, with the upper handle housing 14, the cover disk 40, and the friction-lock knob 22 removed, it is also possible to see a first tension member port 102 and a second tension member port 104 formed through the distal portion of the channeled platform 50. FIG. 5 also shows both a first slider 44 mounted in a first slider trough 46 and a second slider 60 mounted in a second slider trough 48. These troughs 46, 48 are shown to best advantage in FIG. 10. The first tension member anchor 62 is shown mounted on the proximal end of the first slider 44, and a second tension member anchor 106 as shown mounted on the proximal end of the second slider 60.

Figure 6:
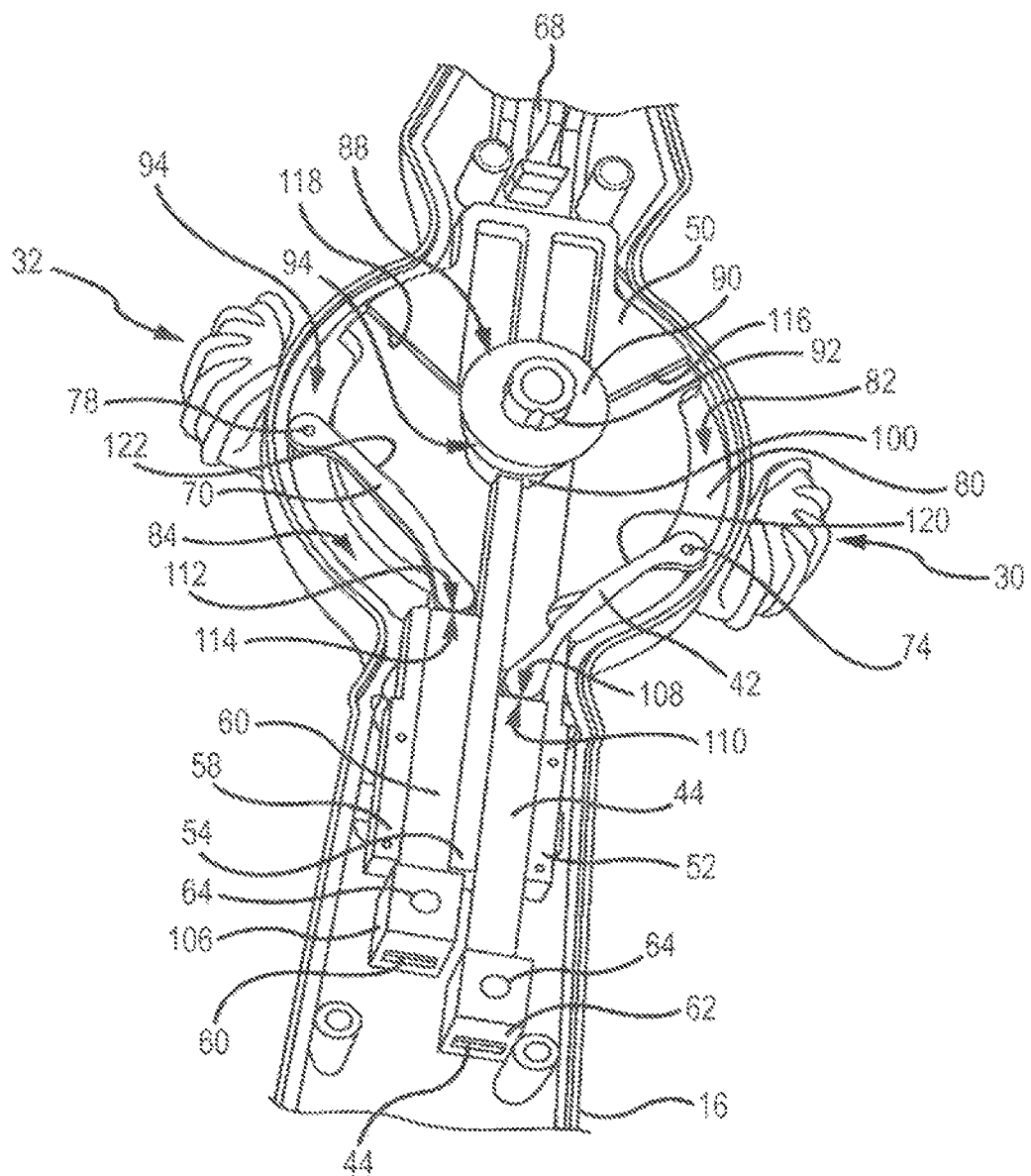
FIG. 6 is an enlarged, fragmentary, isometric view of the deflection actuator depicted in FIG. 5 in a slightly different orientation making clear, for example, the clearance between the tension member anchors.

FIG. 6 is an enlarged, fragmentary, isometric view of the actuator 12 in the configuration also depicted in FIG. 5. However, the viewing angle selected for FIG. 6 better shows the clearance between the first tension member anchor 62 and the second tension member anchor 106, which allows the tension member anchors to move past each other as the deflection actuator is actuated. As shown to good advantage in FIG. 6, the proximal end of the first cam arm 42 includes a first arcuate pushing end 108 adapted to push against a first slider pushed end 110. Similarly the proximal end of the second cam arm 70 also includes a second arcuate pushing end 112 adapted to push against a second slider push end 114. FIG. 6 also clearly shows a first stop wall 116 and a second stop wall 118, both comprising part of the channeled platform 50. These stop walls may be used to help prevent possible over rotation of the deflection actuator. In particular, the first stop wall 116 may, for example, impact a distal side 120 of the first cam arm 42 when the deflection actuator is fully actuated in a first direction (for example, counter-clockwise in FIG. 6); and the second stop wall 118 may impact a distal side 122 of the second cam arm 70 when the deflection actuator 12 is fully actuated in the opposite direction (for example, clockwise in FIG. 6).

Figure 7:
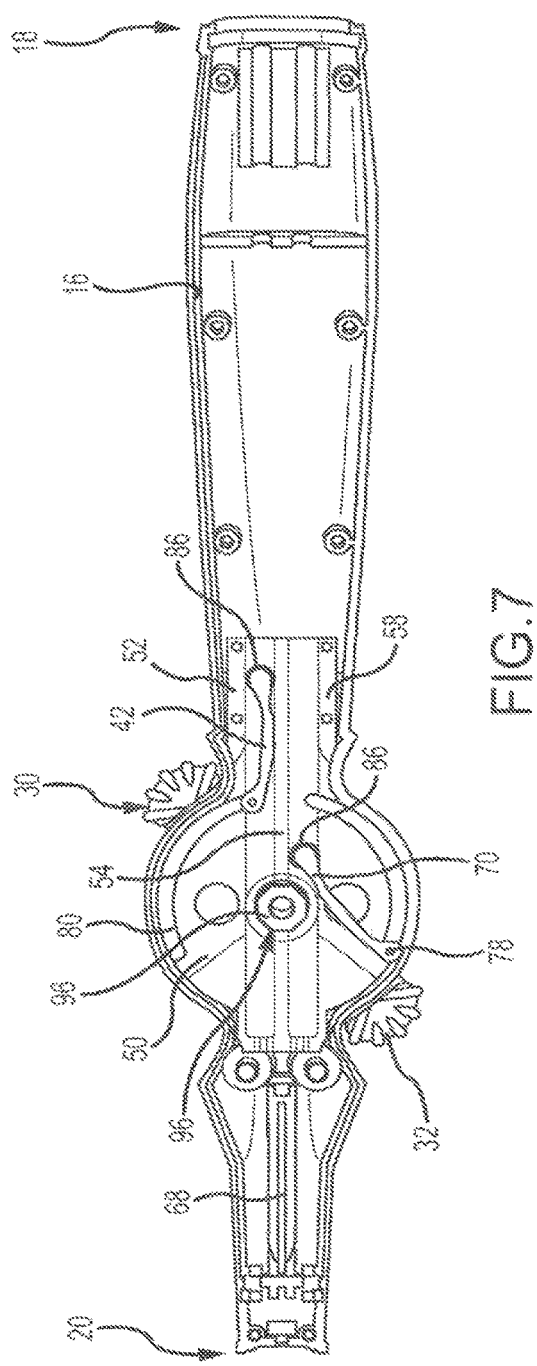
FIG. 7 is a top or plan view of the deflection actuator mounted in the lower handle housing with the friction-lock knob and the knob receiver removed and with the deflection actuator fully actuated in a first direction.

FIG. 7 is a top or plan view, depicting components of the deflection actuator 12 mounted in the lower handle housing 16, and with the deflection actuator fully actuated in a first direction. In this configuration, the first cam arm 42 is displaced as far as possible toward the proximal end 18 of the lower handle housing 16. Simultaneously, the second cam arm 70 is displaced as far as possible, forward toward the distal end 20 of the lower handle housing. The first roller 86 and the second roller 86 are both visible in this figure. As will be discussed further below, these rollers may ride against the walls comprising one of the slider troughs 46, 48 while the associated cam arms 42, 70 press against their respective slider 44, 60.

Figure 8:
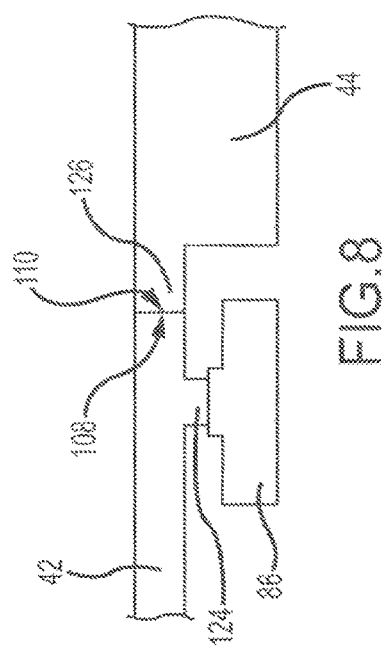
FIG. 8 is an enlarged, fragmentary side view of the proximal end of a cam arm pushing on the distal end of a slider, revealing a slider ledge or overhang that accommodates the roller that is rotatably mounted below the lower surface of the cam arm.

FIG. 8, which is an enlarged, fragmentary view of a proximal portion of the first cam arm 42 and the distal portion of the first slider 44, shows the first roller 86 mounted on a roller pin 124 projecting downwardly from a lower surface of the first cam arm 42. As shown in FIG. 8, the distal end of the first slider may include a first slider ledge or overhang 126 to accommodate the roller 86.

Figure 9:
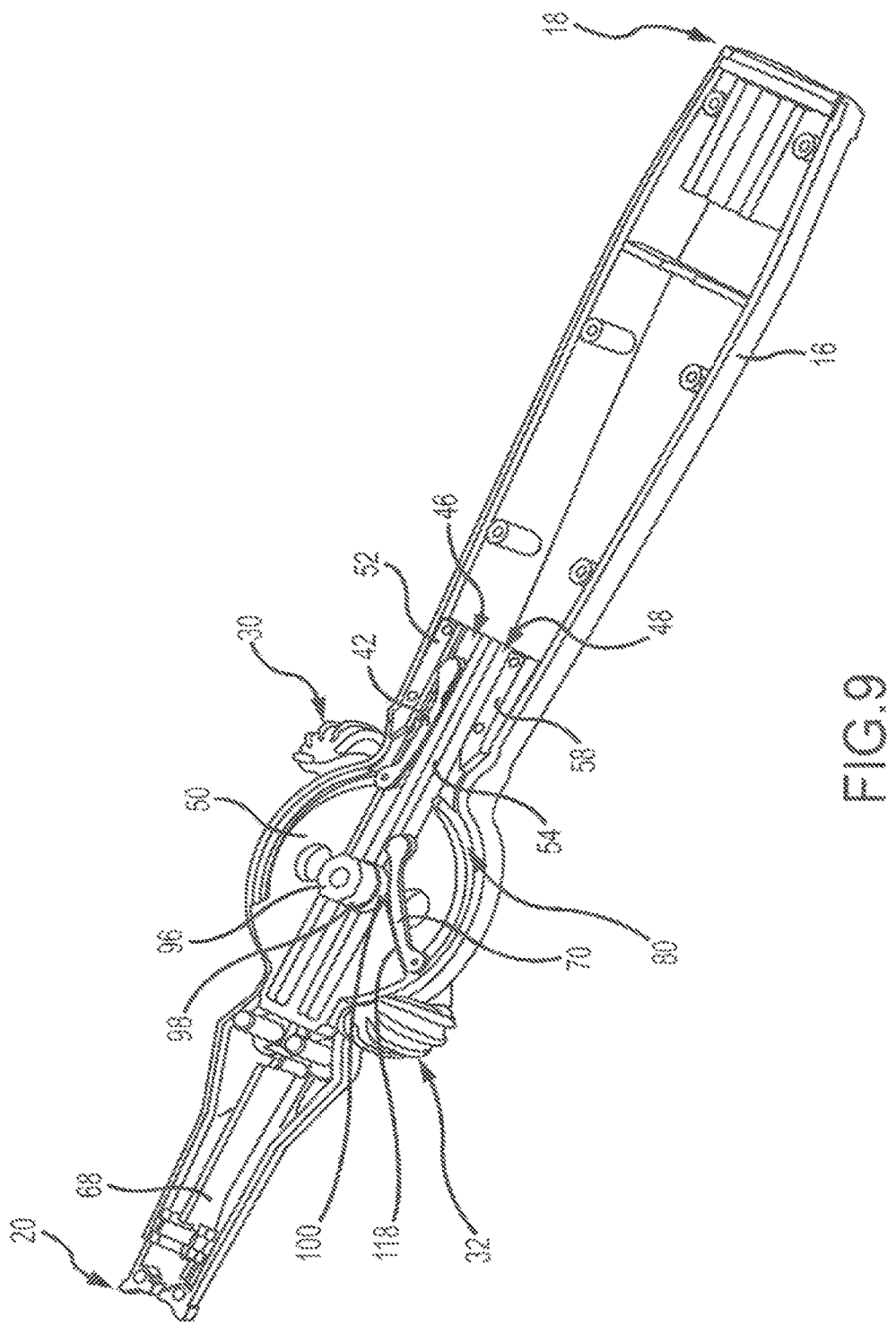
FIG. 9 is an isometric view of the deflection actuator mounted in the lower handle housing and in the orientation also depicted in FIG. 7.

FIG. 9 is an isometric view of the components depicted in FIG. 7 looking downward and at the left or port side of the lower handle housing 16 and various components of the deflection actuator 12. In this figure, the first cam arm 42 is shown riding in the first guide trough 46 between the central wall 54 and the starboard wall 52. The second slider 60 (not shown in FIG. 9) would similarly ride in the second guide trough 48 between the port wall 58 and the central wall 54. As discussed above in connection with FIG. 7, this orientation of the deflection actuator places the first cam arm 42 in its maximum proximal position, and the second cam arm 70 in its maximum distal position.

Figure 10:
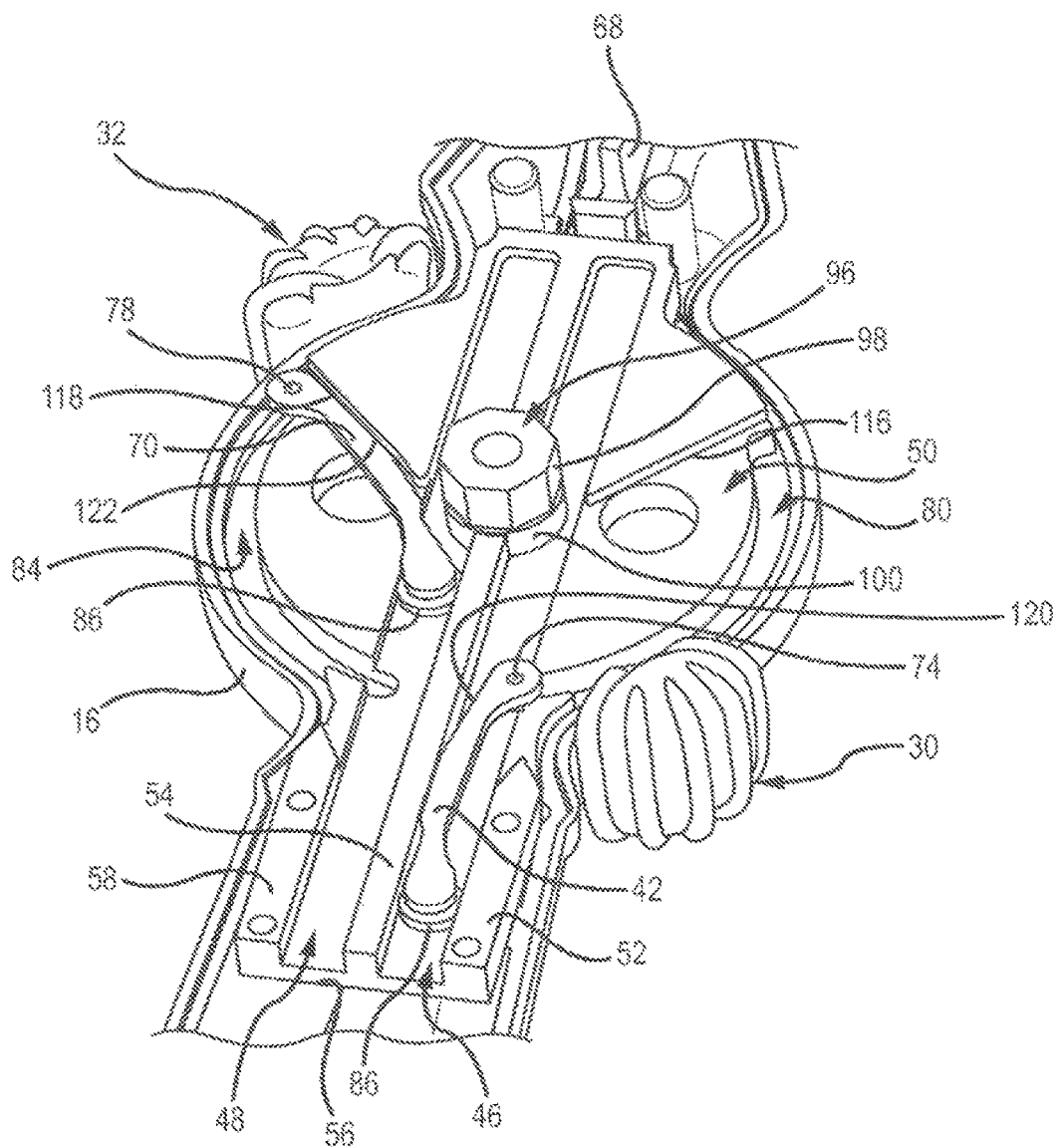
FIG. 10 is an enlarged, fragmentary, isometric view of the deflection actuator in the configuration also shown in FIGS. 7 and 9, but with the sliders removed.

FIG. 10 is an enlarged, fragmentary, isometric view of the deflection actuator components in the state of deflection that is also depicted in FIGS. 7 and 9. In FIG. 10, however, it is easier to see the first roller 86 riding in the first guide trough 46 between the starboard wall 52 and the central wall 54; and the second roller 86 riding in the second guide trough 48 between the port wall 58 and the central wall 54. FIG. 10 also clearly shows the distal side 122 of the second cam arm 70 impacting the second stop wall 118 when the actuator is in this fully-deflected configuration (i.e., rotated fully clockwise as depicted in FIG. 10). As the pivotable base 80 is rotated fully clockwise below the channeled platform 50 by the user putting a proximal force on the first thumb boss 30 and/or a distal force on the second thumb boss 32, the distal end of the first cam arm 42 travels clockwise in an arcuate path to the location depicted in FIG. 10, while the distal end of the second cam arm 70 travels distally in an arcuate path while the second pin block 76 (shown in, for example, FIGS. 3 and 5) rides in the second pin block channel 84 adjacent to or against an arcuate surface of the channeled platform 50. As also clearly shown in FIG. 10, the rollers 86 project more rearwardly or proximally than the proximal ends of each cam arm. This relationship is also shown in the fragmentary view depicted in FIG. 8.

Figure 11:
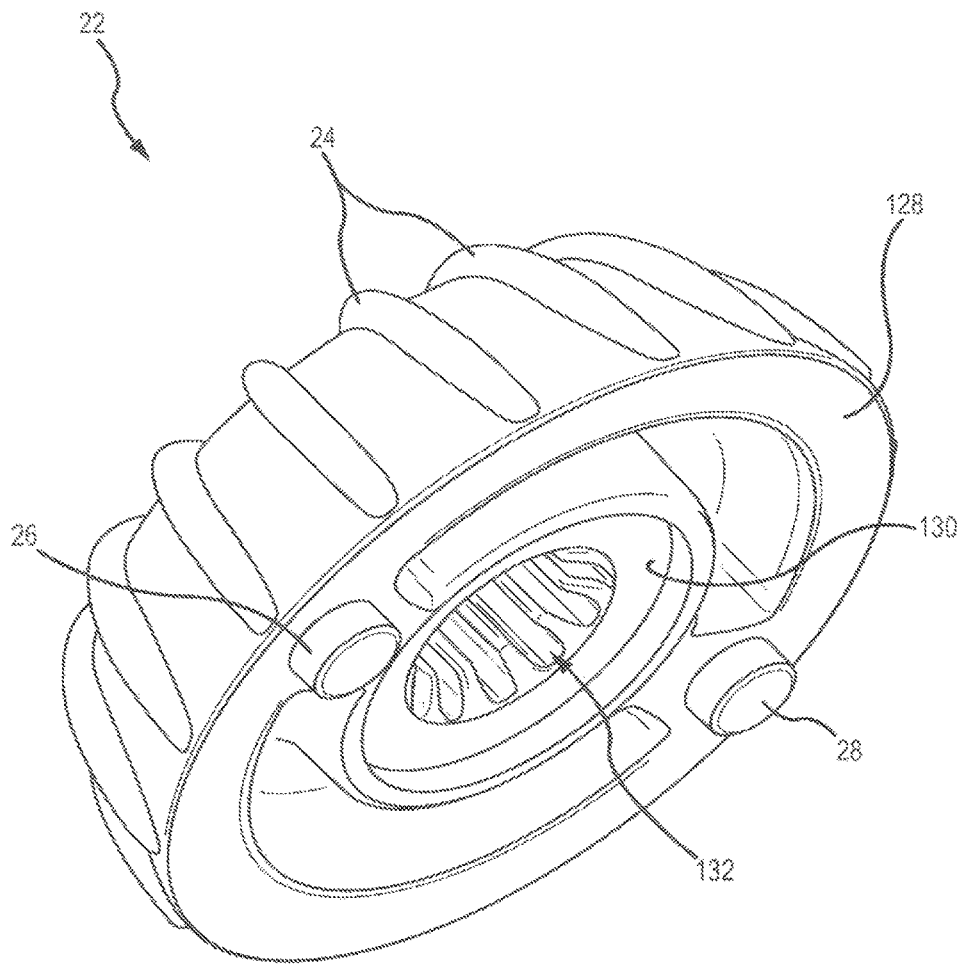
FIG. 11 is an enlarged view showing the underside of the friction-lock knob.

FIG. 11 is an enlarged, isometric view looking toward a lower surface 128 of one possible embodiment of the friction-lock knob 22. As previously mentioned, this knob may comprise a plurality of knob knurls 24 to make it easier for an electrophysiologist, physician, or other user to rotate the friction-lock knob 22, even if wearing a surgical glove. As also mentioned above, the knob may comprise a pair of knob limit pins 26, 28 protruding from its lower surface 128. These limit pins are configured to ride in arcuate or C-shaped channels (not shown) formed into or through the upper handle housing 44. Similar C-shaped channels may be seen in, for example, co-owned U.S. provisional patent application No. 61/820,613, filed on 7 May 2013, and titled, "Handle for Deflectable Catheter," which is hereby incorporated by reference as though fully set forth herein. The C-shaped channels that would be formed in or through the upper handle housing would each accommodate one of these knob limit pins 26, 28. When the friction-lock knob 22 is rotated to the maximum extent in either direction, one or both of the knob limit pins may impact a longitudinal end of one of these C-shaped channels.

Continuing to look at FIG. 11, in the depicted embodiment of the friction-lock knob 22, an annular seat 130 is formed in the underside of the knob. This annular seat is configured to receive the knob support ring 90 comprising part of the knob receiver 88, which is shown in, for example, FIGS. 5, 6, 13, and 14. A splined pocket 132 may also be formed in the underside of the friction-lock knob. This splined pocket 132 is configured to accommodate the splined, knob-mounting shaft 92 that is visible in, for example, FIGS. 5 and 6. The splined pattern depicted in FIGS. 5 and 6 on the splined, knob-mounting shaft 92 is slightly different from the splined pattern depicted in FIG. 11 in the splined pocket 132. A variety of different splined patterns may be used as long as the splined pocket is keyed to the splined, knob-mounting shaft such that rotation of the knob 22 rotates the splined receiver 88.

FIG. 12 depicts an enlarged, isometric view of one embodiment of the pivot hub 96. In this embodiment, the pivot hub includes an upper keyed section 98 extending longitudinally downward from the perimeter of a top or end surface 134 of the pivot hub. The outer surface of the pivot hub 96 may also define an intermediate bearing surface 100 and a lower keyed section 136. The pivot hub depicted in FIG. 12 also includes an annular ledge or 'lifting ledge' 138 positioned above a lower disk 140. Finally, in this embodiment, the pivot hub 96 may also include a pivot shaft 142. Each of these parts of the pivot hub will be described further below in connection with the description of FIGS. 13 and 14.

Figure 13:
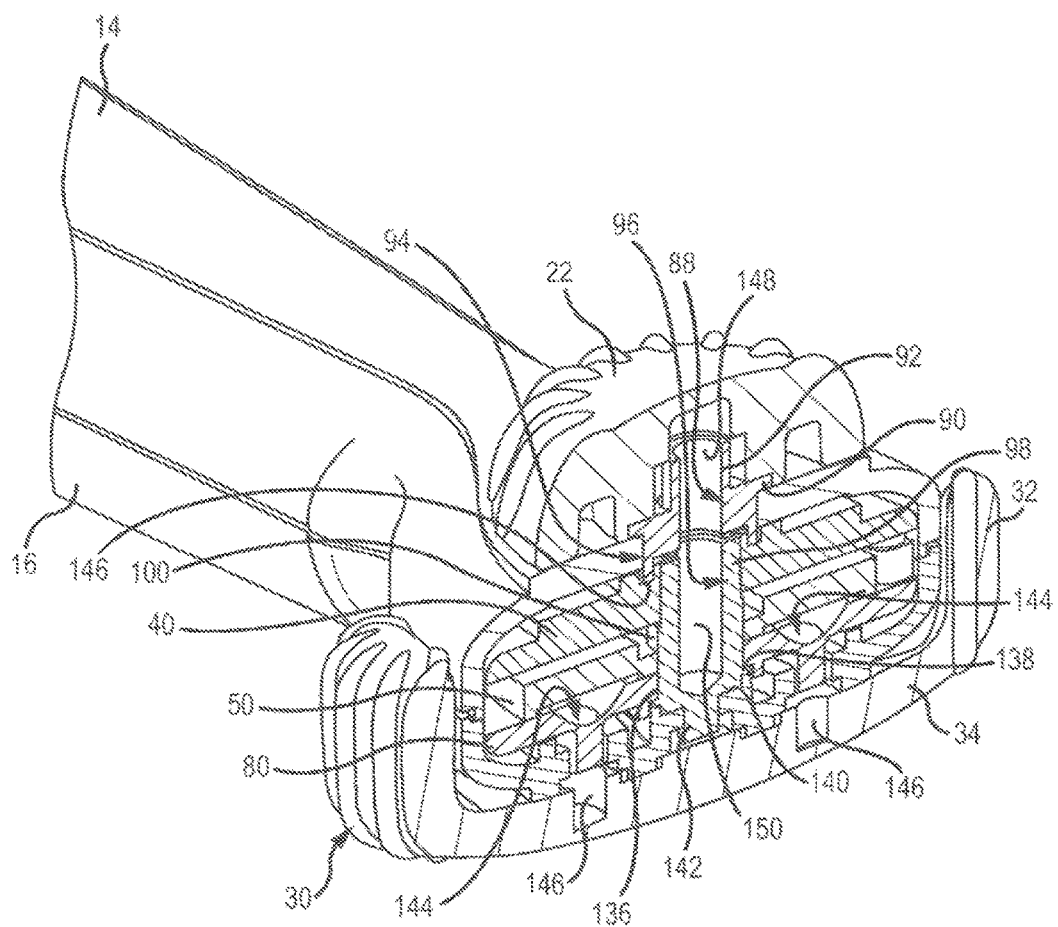
FIG. 13 is a fragmentary, isometric, cross-sectional view taken in the direction of line 13-13 of FIG. 1 with some components removed, revealing the inner workings of the friction lock.

FIG. 13 is an enlarged, fragmentary, cross-sectional view taken along line 13-13 in FIG. 1, effectively cutting the catheter handle 10 and deflection actuator 12 in half laterally. In this figure, some components have been removed for clarity and easier comprehension. For example, when the handle is fully assembled, the pivotable base 80 would be connected to the crossmember 34 such that when a user displaces the thumb bosses 30, 32, the crossmember 34 would, in turn, rotate the pivotable base 80 since screws or pins would attach the crossmember to the pivotable base. Screws (not shown) could, for example, be mounted in the depicted channels 144 through the pivotable base 80 and threaded into blind holes 146 formed in the crossmember 34. Such mounting screws have not been shown in FIGS. 13 and 14 for clarity.

Working from top to bottom in FIG. 13, it is possible to see the friction-lock knob 22 mounted on top of the knob receiver 88. In particular, the knob-mounting shaft 92 is mounted in the splined pocket 132 (labeled in, for example, FIGS. 11 and 14) comprising part of the friction-lock knob 22. The knob may be, for example, press-fit or adhered onto the knob receiver 88 during assembly. As shown in this figure, once the friction-lock knob is assembled with the knob receiver, the knob support ring 90 rides in the annular seat 130 (labeled in FIG. 11). The lower surface 128 of the friction-lock knob and the lower surface of the knob support ring 90 are shown riding on the upper surface of the upper handle housing 14 in FIG. 13. Also, the lower body 94 of the knob receiver 88 is shown projecting through a hole through the upper handle housing 14, and a lower surface (i.e., a downwardly-pressing surface) 146 of the knob receiver 88 is shown pivotably riding on the top surface of the cover disk 40.

The pivot hub 96 is also visible in FIG. 13 in cross section. As shown, the top surface 134 (labeled in FIG. 12) of the pivot hub is displaced/offset from the knob receiver for reasons that are apparent from the below discussion. A threaded member (not shown) would be mounted in a central hole 148 in the knob receiver 88 and thread into a central hole (or blind hole) 150 in the pivot hub 96. Since, as previously discussed, rotation of the friction-lock knob 22 rotates the knob receiver 88, this would, in turn, also rotate the threaded member fixedly mounted in the hole 148 in the knob receiver, thereby threading the threaded member into the blind hole 150 of the pivot hub 96. As already noted, the downwardly-pressing surface 146 of the knob receiver presses on an upper surface of the cover disk 40. The cover disk, in turn, rides on an upper surface of the channeled platform 50. The channeled platform, in turn, rides on an upper surface of the pivotable base 80. In the embodiment depicted in FIG. 13, the pivotable base includes portions that project through the slots in the lower handle housing 16. The upper keyed section 98 of the pivot hub 96 is keyed to the hole through the center of the cover disk 40. Thus, the pivot hub does not rotate relative to the cover disk. Similarly, the lower keyed section 136 of the pivot hub 96 is keyed to the pivotable base 80. As a result, the pivot hub 96, the cover disk 40, the pivotable base 80, and the cross member 34 and thumb bosses 30, 32, all rotate together.

During operation of the deflection actuator 12, the user would rotate the deflection actuator by applying pressure to one or both of the thumb bosses 30, 32. Once the actuator was rotated a desired amount, the user could rotate the friction-lock knob 22 to hold the actuator in that rotated configuration, which would maintain, for example, a desired deflection of the distal end of the catheter shaft (not shown). For example, when the friction-lock knob 22 is rotated clockwise, that would rotate the knob receiver clockwise, which, in turn, would rotate the threaded member (not shown) that is fixedly mounted in the central hole 148 of the knob receiver 88 clockwise. Rotation of the threaded member in the blind hole 150 in the center of the pivot hub 96 would pull or lift the pivot hub upwardly toward the knob receiver 88 and the friction-lock knob 22. As the pivot hub is lifted, the lifting ledge 138 is lifted upwardly against the lower surface of the pivotable base 80, which, in turn, would lift upwardly on the lower surface of the channeled platform 50, which, in turn, would lift upwardly on the lower surface of the cover disk 40. As a result, the cover disk 40, the channeled platform 50, and the pivotable base 80 get pinched or clamped together between the upwardly-moving lifting ledge 138 (which lifts upwardly on the lower surface of the pivotable base 80) and the downwardly-pressing surface 146 of the knob receiver 80 (which presses downwardly on the upper surface of the cover disk 40). Once sufficient friction is achieved, the deflection actuator is held in a desired state of deflection, even if the physician or other user completely removes his or her hands from the catheter. Similarly, when the physician or other user applies rotational pressure to the thumb bosses 30, 32, that rotates the pivotable base 80, which, as noted above, is keyed to the lower keyed section 136 of the pivot hub 96.

Figure 14:
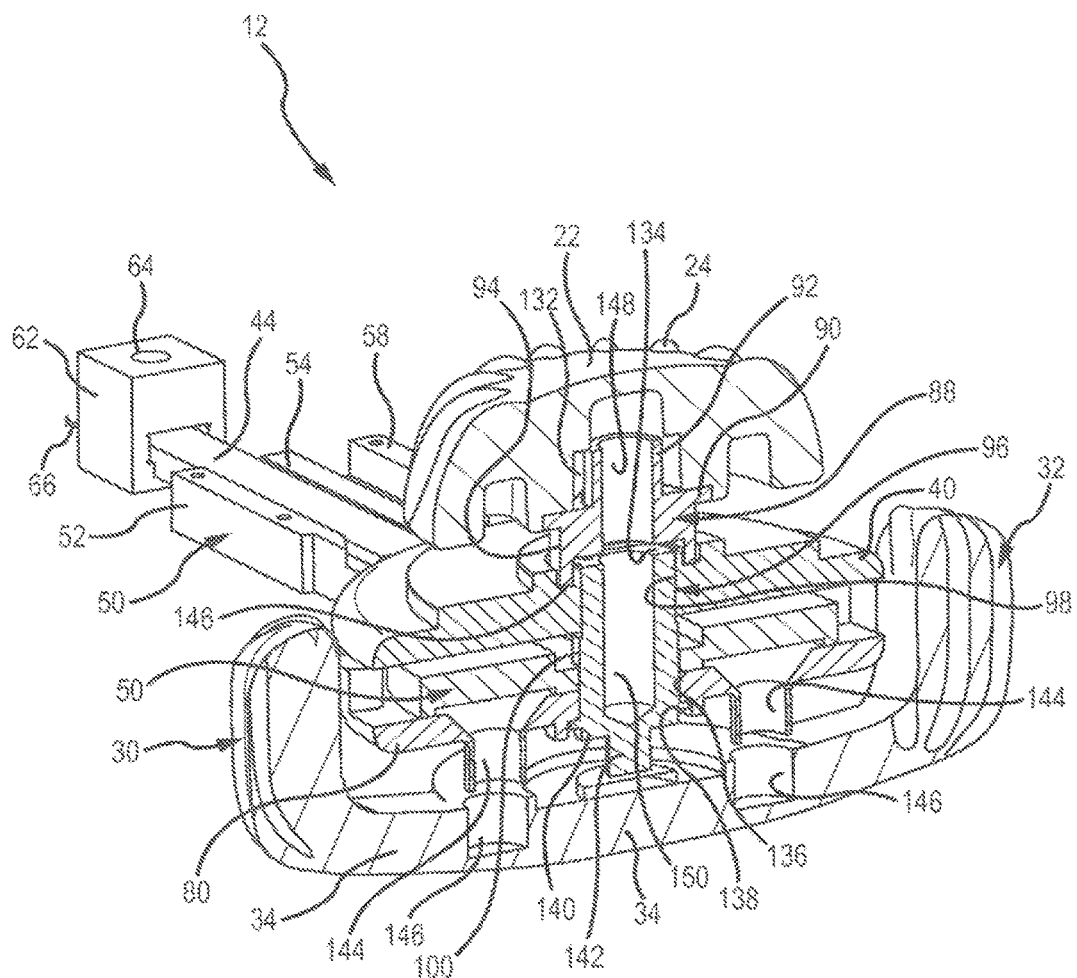
FIG. 14 is similar to FIG. 13, but depicts the actuator removed from both the upper handle housing and the lower handle housing.

FIG. 14 is similar to FIG. 13. However, in FIG. 14, both the upper handle housing 14 and the lower handle housing 16 have been removed. This figure, therefore, shows most components of an embodiment of the deflection actuator 12, separated from the handle housings. As clearly shown in this figure when considered in view of FIG. 12, the intermediate bearing surface 100 of the pivot hub 96 slippingly rides in a hole through the channeled platform 50. Thus, the pivot hub is able to rotate relative to the channeled platform. In contrast, and as also visible in FIG. 14 and as discussed above in connection with FIG. 13, the cover disk 40 rides on the upper keyed section 98 of the pivot hub 96. Thus, the cover disk 40 rotates with the pivot hub 96. Similarly, the pivotable base 80 is keyed to the lower keyed section 136 of the pivot hub 96 and, therefore, also pivots with the pivot hub. As a result, and as already noted above, when the thumb bosses 30, 32 and crossmember 34 are rotated in either direction by the user of the catheter, the pivotable base 80, the pivot hub 96, and the cover disk 40 rotate together. This, in turn, results in the knob receiver 88 and knob 22 also possibly rotating with the cover disk, the pivot hub, the pivotable base, and the crossmember and thumb bosses. As a result, the amount of 'locking friction' present in the friction lock may not change while the physician or other user manipulates the distal end of a catheter by actuating the deflection actuator via varying pressure on one or both of the thumb bosses. If the knob receiver 88 and the knob 22 do not rotate when the thumb bosses 30, 32 and crossmember 34 are pivoted (for example, if there is insufficient friction between the top surface of the cover disk 40 and the downwardly-pressing surface 146), the blind hole 50 can merely thread onto (and off of) the threaded member (not shown) fixedly mounted in the hole 148 through the knob receiver 88.

Once the desired amount of catheter deflection is achieved, the user, while holding the thumb bosses 30, 32 and crossmember 34 in place, rotates the friction-lock knob 22. This rotation of the friction-lock knob, as previously discussed, turns the knob receiver 88 and the threaded member mounted in the hole 148 through the knob receiver. As that threaded member threads into the blind hole 150 in the pivot hub 96, the pivot hub is lifted toward the friction-lock knob or pushed away from the friction-lock knob, depending upon which direction the user rotates the friction-lock knob. If the user is attempting to increase the friction, the cover disk 40, the channeled platform 50, and the pivotable disk 80 are pinched or clamped together until the distal end of the catheter shaft is held in the desired state of deflection. When the physician is ready to change the deflection of the catheter shaft, the friction-lock knob is rotated in the opposite direction, thereby relieving the friction between various components comprising the deflection actuator 12.

Figure 15:
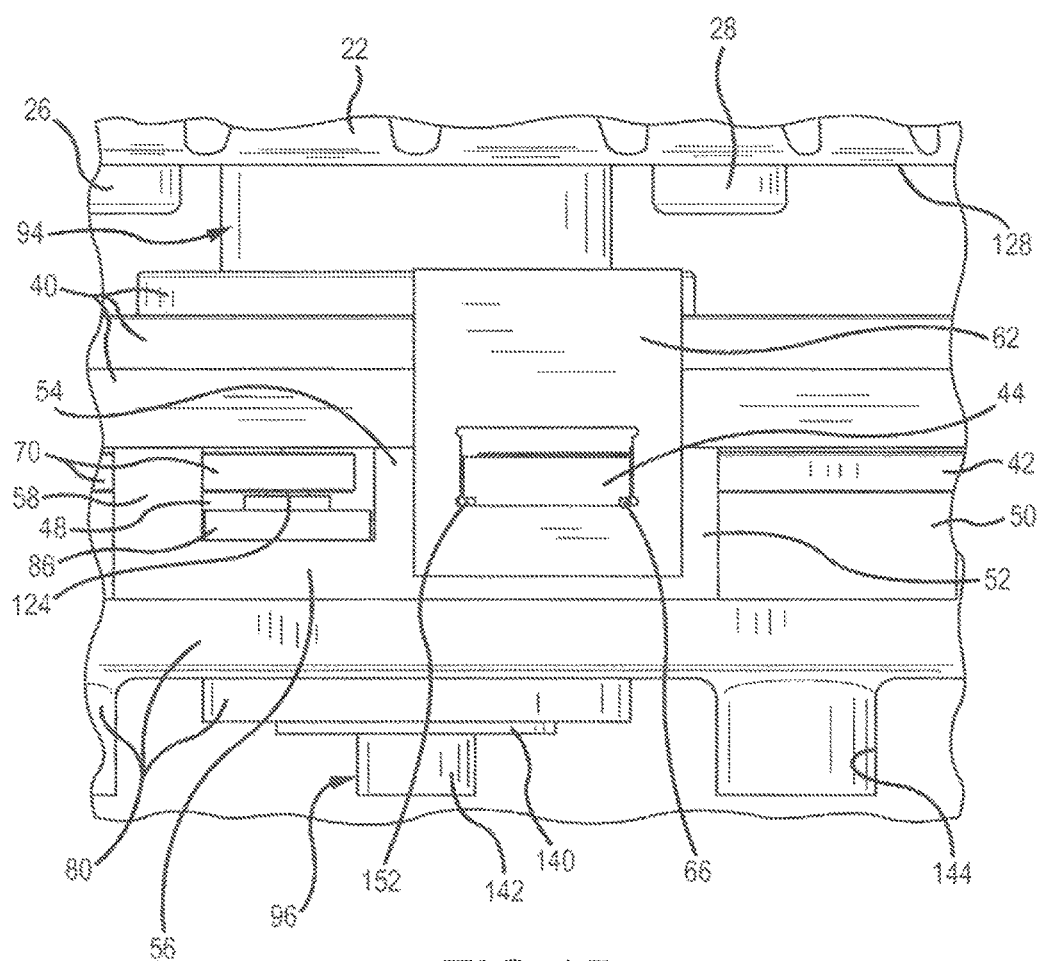
FIG. 15 is a fragmentary view taken in the direction of line 15-15 of FIG. 2, depicting various components of the deflection actuator according to an embodiment.

FIG. 15 is an enlarged, fragmentary view looking in the direction of line 15-15 in FIG. 2. At the top of FIG. 15, a portion of the friction-lock knob 22 may be seen. At least a portion of the two knob limit pins 26, 28 that are fully visible in FIG. 11 may be seen in FIG. 15 projecting downwardly from the lower surface 128 of the friction-lock knob. Since, in this figure, the knob is mounted on the knob receiver, it is also possible to see the lower body 94 of the knob receiver projecting upwardly toward the lower surface 128 of friction-lock knob 22 in FIG. 15. Moving further downward in FIG. 15, it is also possible to see the cover disc resting on top of the port wall 58, the central wall 54, and the starboard wall 52, which comprise part of the channeled platform 50. The second cam arm 70 is visible in the middle of the left-hand side of FIG. 15. Between the port wall 58 and the central wall 54 comprising part of the second slider trough 48, it is possible to see a proximal end of the second cam arm 70 and a short section of the roller pin 124 projecting downwardly from the lower surface of the second cam arm. The second roller 86 is mounted on this second roller pin so as to roll between the port wall and the central wall. A portion of the first cam arm 42 is also visible.

Toward the center of FIG. 15 it is possible to see the first tension member anchor 62 mounted on the first slider 44. As clearly shown in this figure, in this embodiment, there are longitudinally-extending tension member notches 152 formed along the lower inboard and outboard longitudinal edges of the first slider 44. Only the inboard tension member notch is labeled in FIG. 15 since the first tension member 66 is riding in the outboard tension member notch in this figure. Similar notches would be formed on the second slider 60 (not shown in this figure). In FIG. 15, the lower right-hand notch has the first tension member 66 riding in it. When the first tension member anchor 62 is attached to the first slider 44, the first tension member gets pinched between the first tension member anchor and the tension member notch so that, when the first slider moves longitudinally in the catheter housing (e.g., parallel or substantially parallel to longitudinal axis 38 shown in FIG. 1), the first tension member anchor ensures that longitudinal forces on the first slider get transferred to the first tension member. In FIG. 15, the pivotable base 80, as shown below the channeled platform 50, includes a pair of pin or screw towers defining screw channels 144 and projecting downwardly from a lower surface of the pivotable base 80. These towers are configured to project or extend through the lower handle housing 16 and are configured to accommodate the pins or screws that mount the pivotable base 80 to the crossmember 34 as discussed above. Finally, the lower disc 140 and pivot shaft 142 of the pivot hub 96 may also be seen in the bottom central portion of FIG. 15.

Figure 16:
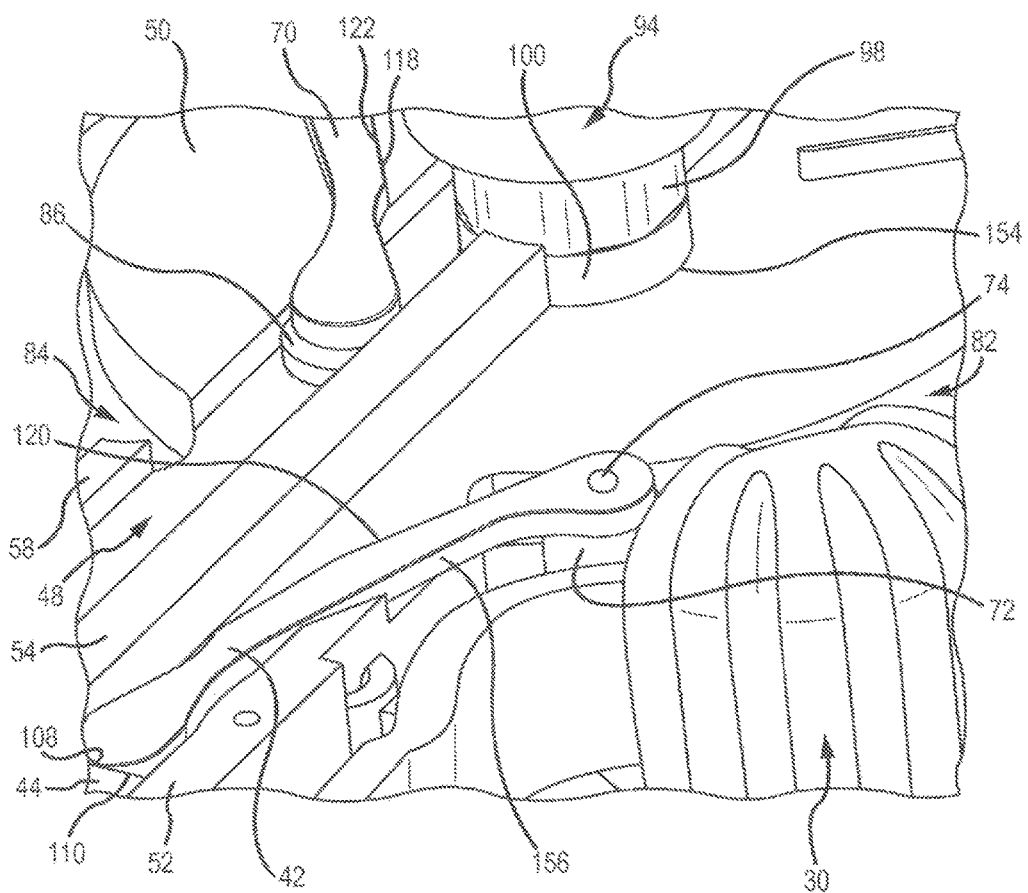
FIG. 16 is a greatly enlarged, fragmentary, isometric view of select components of a deflection actuator in roughly the same configuration shown in FIG. 4.

FIG. 16 is an enlarged, fragmentary, isometric view of an upper, central portion of the deflection actuator. In this figure, the deflection actuator is in a position that is similar to the position shown in FIG. 4. The lower body 94 of the knob receiver 88 is shown at the top center portion of FIG. 16. It is also possible to see the upper keyed section 98 and the bearing surface 100 of the pivot hub 96. The bearing surface is shown passing through a central hole 154 through the channeled platform 50. A portion of the second cam arm 70 is shown with its distal side 122 against the second stop wall 118 of the channeled platform 50. The second roller 86 is pivotably mounted to the proximal end of the second cam arm 70, and is shown rotatably riding in the second slider trough 48. A fragment of the second pin block channel 84 is visible in the upper left portion of FIG. 16. The first cam arm 42 is shown in its most proximal position. The first arcuate pushing end 108 of the first cam arm 42 is shown pushing against the first slider pushed end 110, near the lower left-hand corner of FIG. 16. The proximal side 156 of the first cam arm 42 is depicted nearly contacting a distal portion of the starboard wall 52. The distal end of the first cam arm is shown pivotably mounted on a first pivot pin 74 to the first pin block 72. Near the middle of the right-hand portion of FIG. 16, a fragment of the first pin block channel 82 may be seen.

Figure 17:
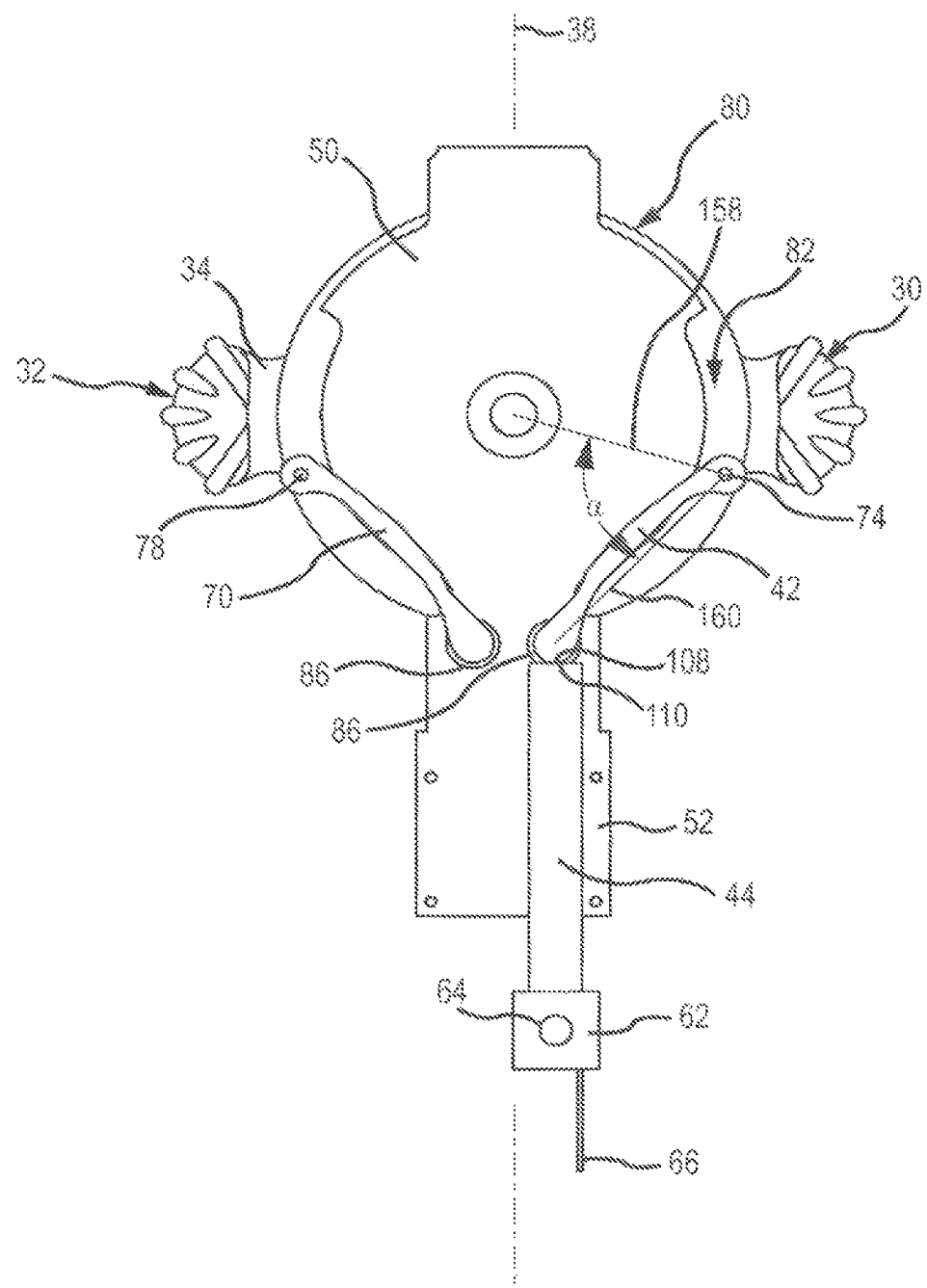
FIGS. 17-19 schematically depict components of a deflection actuator moving from a neutral position shown in FIG. 17 to a fully-actuated configuration shown in FIG. 19.
Figure 18:
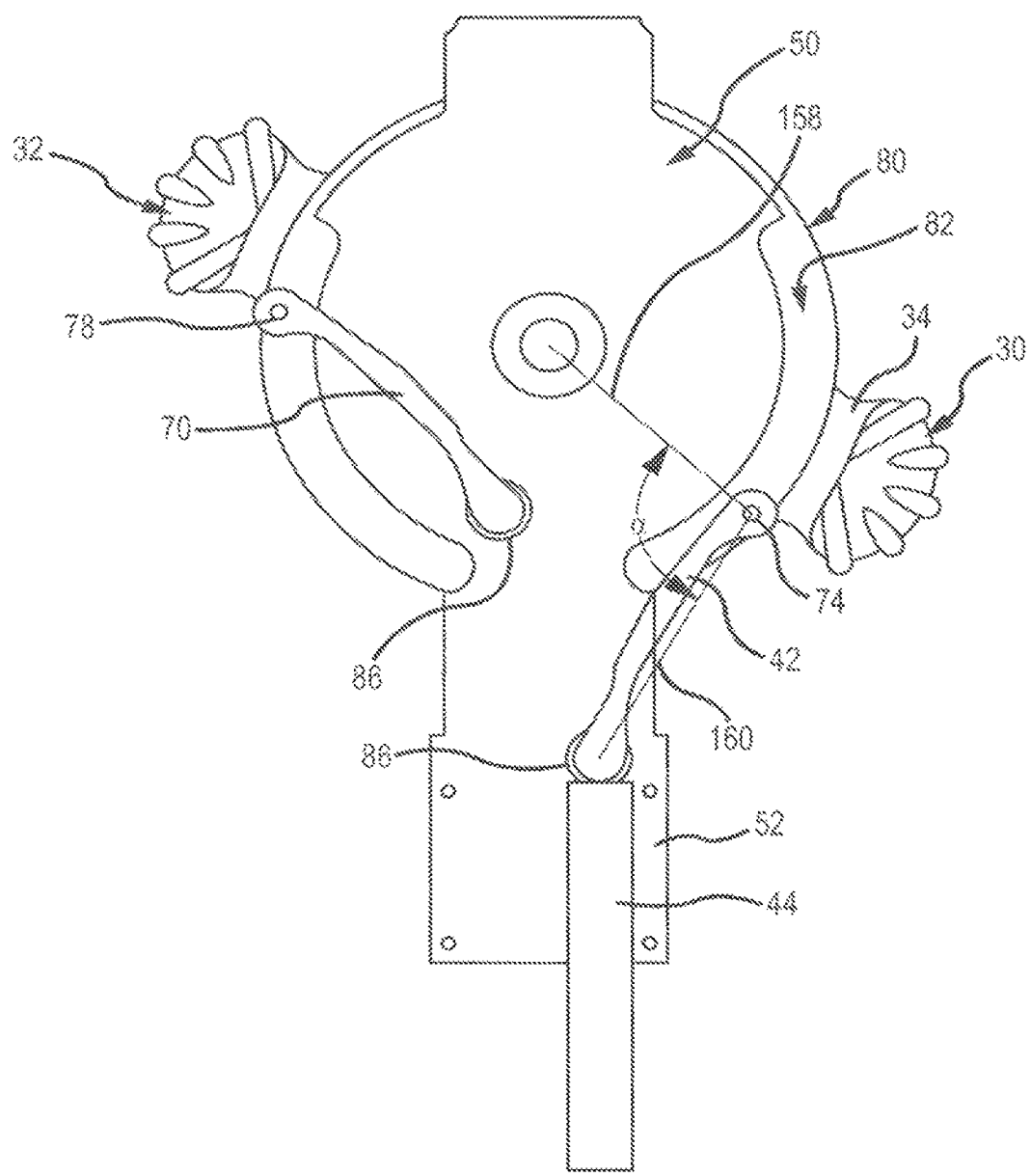
Figure 19:
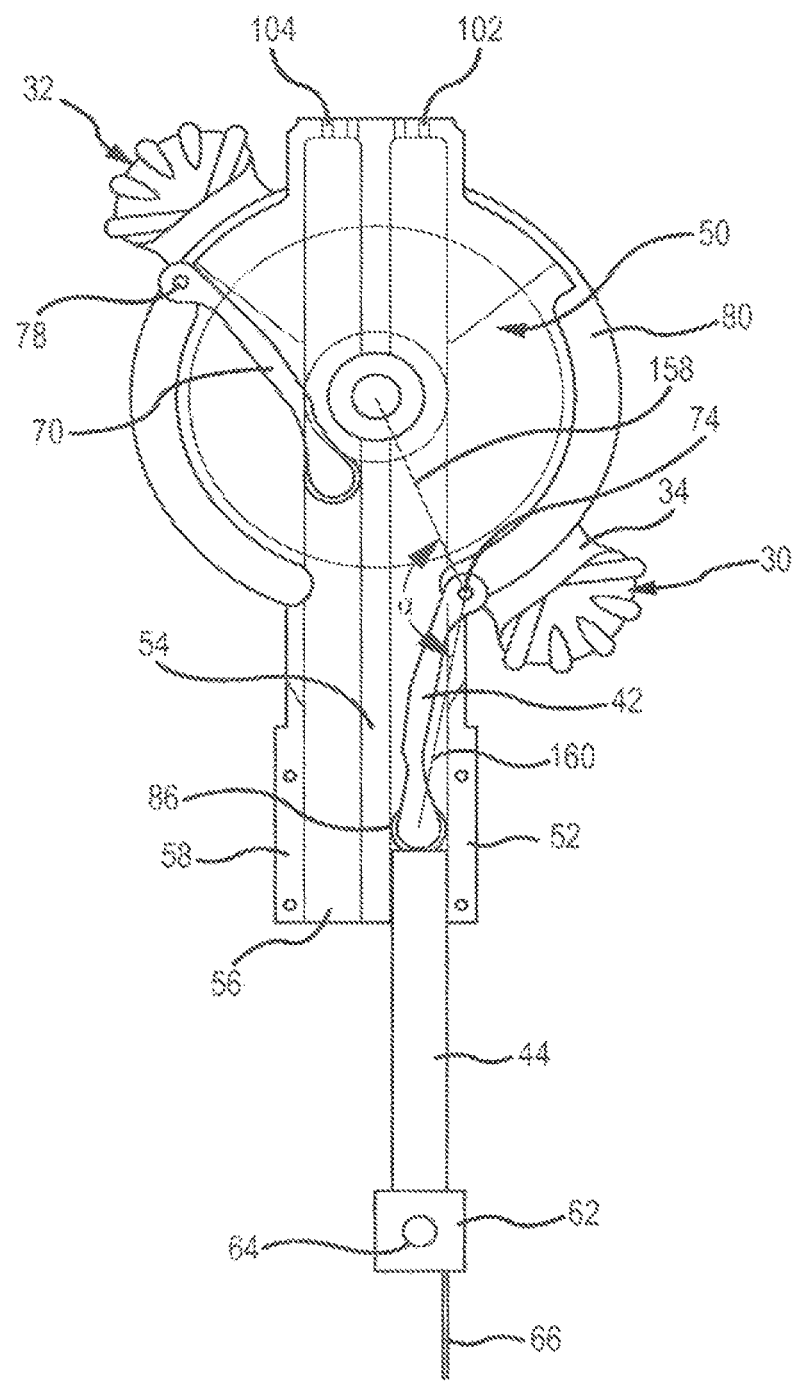

Referring next to FIGS. 17-19, the mechanical advantage achieved by this embodiment of the deflection actuator is described next. For easier comprehension, each of these three figures schematically depicts only a limited number of the components comprising the deflection actuator 12. FIG. 17 depicts the actuator in a neutral configuration. In this configuration or state of catheter shaft deflection, the various components of the deflection actuator are symmetrically distributed on either side of the catheter handle's longitudinal axis 38. For example, the first and second thumb bosses 30, 32 are symmetrically positioned across from each other, one in the 3 o'clock position and the other in the 9 o'clock position in this figure.

The first cam arm 42 and the second cam arm 70 are both shown in each of FIGS. 17-19. Also shown in each of these figures is a first line 158 extending from the axis of rotation of the deflection actuator through the axis of rotation of the first pivot pin 74. Similarly, a second line 160 is shown extending between the axis of rotation of the first pivot pin 76 and the axis of rotation of the roller pin 124 at the proximal end of the first cam arm. Angle α is defined between the first line 158 and the second line 160. Comparing FIG. 18 to FIG. 17, the actuator in FIG. 18 has been rotated slightly clockwise from its position shown in FIG. 17. This clockwise rotation of the actuator drives the first pivot pin 74 in an arcuate path defined by the first pin block channel 82 (see also, for example, FIG. 4). As the first cam arm 42 is driven proximally by this clockwise rotation of the actuator, the angle α is increasing.

Looking now at FIG. 19, the actuator has been further rotated clockwise to a fully-actuated configuration. In this configuration, the first slider 40 has been driven or pushed proximally to its maximum amount, putting the maximum amount of proximal tension in the first tension member 66. With the actuator in this configuration, the distal end of the catheter would be deflected the maximum amount to a first side.

Continuing to look at FIG. 17-19, as the actuator moves from the neutral configuration depicted in FIG. 17, through the partially-actuated configuration depicted in FIG. 18, and into the fully-actuated configuration depicted in FIG. 19, the distal end of the catheter shaft (not shown) is being progressively deflected to a greater extent. Thus, the tension in the tension member 66 is increasing from the configuration shown in FIG. 17 to the configuration shown in FIG. 18, and then to the configuration shown in FIG. 19. As may be seen, however, by looking at FIG. 17-19, as the tension in the tension member increases, so does the mechanical advantage provided by the deflection actuator. As a result, the thumb force felt by the user remains manageable and tailorable to a user's preference. By changing, for example, the size, shape, or diameter of the pivotable base 80, the length and shape of the cam arms 42, 70, and the location of each cam arm pivot pin 74, 78, it is possible to control and tailor the force profile experienced by a user of the deflection actuator as the tension in the tension members increases or decreases during use of the catheter.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of all embodiments.

Reference throughout the specification to "various embodiments," "some embodiments," "one embodiment," or "an embodiment," or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation, provide that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial or directional terms such as "vertical," "horizontal," "up," "down," "clockwise," and "counterclockwise" may be used herein with respect to the illustrated embodiments. However, medical instruments may be used in many orientations and positions, and these terms are not intended to be limiting and absolute.

Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relation to each other. As used herein, joinder references may also include two components that are molded as a single or unitary piece. Changes in detail or structure may be made without departing from the spirit of the disclosure as defined in the appended claims.

What is claimed is:

1. A deflection actuator comprising:
   a channeled platform adapted to be fixedly mounted to a catheter handle housing, wherein the channeled platform comprises a first slider trough;
   a pivotable base arranged in a stacked configuration with the channeled platform and adapted to pivot relative to the channeled platform;
   a first slider slidably mounted in the first slider trough;
   a first cam arm pivotally connected to the pivotable base and adapted to push the first slider in the first slider trough upon pivotable motion of the pivotable base relative to the channeled platform;
   a cover disk, wherein the channeled platform is sandwiched between the cover disk and the pivotable base; and
   a pivot hub rotatably mounted in a hole through the channeled platform for rotation relative to the channeled platform, wherein the pivot hub comprises a first keyed section keyed to the pivotable base and a second keyed section keyed to the cover disk such that the pivot hub, the pivotable base, and the cover disk rotate together.

2. The deflection actuator of claim 1 further comprising a friction-lock knob, wherein the friction-lock knob is adapted to rotate relative to the channeled platform to control friction between the channeled platform and the pivotable base.

3. The deflection actuator of claim 2, wherein the channeled platform defines a first surface, wherein the pivotable base defines a second surface that is parallel to and rides against the first surface.

4. The deflection actuator of claim 2 further comprising a knob receiver, wherein the friction-lock knob is fixedly attached to the knob receiver, wherein the knob receiver comprises a downwardly-pressing surface adapted to press on an upper surface of the channeled platform upon rotation of the friction-lock knob in a first direction.

5. The deflection actuator of claim 4, wherein the knob receiver comprises a knob support ring and a knob-mounting shaft, wherein the friction-lock knob comprises an annular knob seat and a pocket, wherein the knob support ring is mounted in the annular knob seat, and wherein the knob-mounting shaft is mounted in the pocket.

6. The deflection actuator of claim 1 further comprising:
   a friction-lock knob, wherein the friction-lock knob is adapted to rotate relative to the channeled platform to selectably clamp the channeled platform between the cover disk and the pivotable base; and
   a knob receiver, wherein the friction-lock knob is fixedly attached to the knob receiver, wherein the knob receiver comprises a downwardly-pressing surface adapted to press on an upper surface of the cover disk upon rotation of the friction-lock knob in a first direction.

7. The deflection actuator of claim 1 further comprising:
   a second slider trough comprising part of the channeled platform,
   a second slider slidably mounted in the second slider trough,
   a second cam arm pivotally connected to the pivotable base and adapted to push the second slider in the second slider trough upon pivotable motion of the pivotable base relative to the channeled platform.

8. The deflection actuator of claim 7, further comprising:
   a crossmember fixedly attached to the pivotable base; and
   a first thumb boss and a second thumb boss, where the first and second thumb bosses are attached to or comprise an integral part of the crossmember.

9. The deflection actuator of claim 1 further comprising a first tension member anchor adapted to selectably anchor a first tension member to the first slider.

10. The deflection actuator of claim 1, wherein the first slider further comprises a slider pushed end, and wherein the first cam arm comprises an arcuate pushing end adapted to press against the slider pushed end.

11. The deflection actuator of claim 1 further comprising (i) a second slider trough formed in the channeled platform, (ii) a second slider slidably mounted in the second slider trough, and (iii) a second cam arm pivotally connected to the pivotable base and adapted to push the second slider in the second slider trough upon pivotable motion of the pivotable base relative to the channeled platform.

12. The deflection actuator of claim 11, wherein the first cam arm comprises a first end that is pivotally mounted to a first pin block on the pivotable base, and wherein the second cam arm comprises a first end that is pivotally mounted to a second pin block on the pivotable base.

13. The deflection actuator of claim 12,
   wherein the first cam arm further comprises a second end, wherein a first roller is rotatably mounted to the second end of the first cam arm, and wherein the first roller is adapted to roll in the first trough; and
   wherein the second cam arm further comprises a second end, wherein a second roller is rotatably mounted to the second end of the second cam arm, and wherein the second roller is adapted to roll in the second trough.

14. A deflection actuator comprising:
   a pivot hub comprising an end surface, an upper keyed surface, an intermediate bearing surface, a lower keyed surface, and a screw-member-receiving hole oriented along a pivot hub longitudinal axis;
   a cover disk comprising a cover disk central hole mounted on the upper keyed surface of the pivot hub, whereby the pivot hub is adapted to rotate with the cover disk;
   a pivotable base comprising a pivotable base central hole mounted on the lower keyed surface of the pivot hub, whereby the pivot hub is adapted to rotate with the pivotable base;
   a channeled platform adapted to be fixedly mounted to a catheter handle housing, the channeled platform comprising (i) a slider trough and (ii) a channeled platform central hole pivotably mounted on the intermediate bearing surface of the pivot hub, whereby the pivot hub is adapted to freely rotate in the channeled platform central hole;

a knob receiver mounted above the end surface of the pivot hub;

a friction-lock knob mounted on the knob receiver;

a slider comprising a proximal end and a distal end, the slider slidably mounted in the slider trough; and a cam arm comprising a proximal end and a distal end, wherein the distal end of the cam arm is pivotally connected to the pivotable base, wherein the proximal end of the cam arm is adapted to push the distal end of the slider in the slider trough upon pivotable motion of the pivotable base relative to the channeled platform.

15. The deflection actuator of claim 14 further comprising a tension member anchor mounted on the proximal end of the slider.

16. The deflection actuator of claim 14, wherein the proximal end of the cam arm comprises an arcuate pushing end, wherein the distal end of the slider comprises a slider pushed end, and wherein the arcuate pushing end is arranged to push against the slider pushed end.

17. The deflection actuator of claim 14, wherein the pivot hub further comprises an annular lifting ledge adapted to selectably press on the pivotable base to increase friction among the pivotable base, the channeled platform, and the cover disk upon rotation of the friction-lock knob.

18. A deflection actuator comprising:
a channeled platform adapted to be fixedly mounted to a catheter handle housing, wherein the channeled platform comprises a first slider trough;
a pivotable base mounted adjacent to the channeled platform and adapted to pivot relative to the channeled platform;
a first slider slidably mounted in the first slider trough;
a first cam arm pivotally connected to the pivotable base and adapted to push the first slider in the first slider trough upon pivotable motion of the pivotable base relative to the channeled platform;
a cover disk, wherein the channeled platform is sandwiched between the cover disk and the pivotable base; and
a pivot hub rotatably mounted in a hole through the channeled platform for rotation relative to the channeled platform, wherein the pivot hub comprises a first keyed section keyed to the pivotable base and a second keyed section keyed to the cover disk such that the pivot hub, the pivotable base, and the cover disk rotate together.

19. The deflection actuator of claim 18 further comprising a friction-lock knob, wherein the friction-lock knob is adapted to rotate relative to the channeled platform to control friction between the channeled platform and the pivotable base.

20. The deflection actuator of claim 19, wherein the channeled platform defines a first surface, wherein the pivotable base defines a second surface that is parallel to and rides against the first surface.

21. The deflection actuator of claim 19 further comprising a knob receiver, wherein the friction-lock knob is fixedly attached to the knob receiver, wherein the knob receiver comprises a downwardly-pressing surface adapted to press on an upper surface of the channeled platform upon rotation of the friction-lock knob in a first direction.

22. The deflection actuator of claim 21, wherein the knob receiver comprises a knob support ring and a knob-mounting shaft, wherein the friction-lock knob comprises an annular knob seat and a pocket, wherein the knob support ring is mounted in the annular knob seat, and wherein the knob-mounting shaft is mounted in the pocket.

23. The deflection actuator of claim 18 further comprising:
a friction-lock knob, wherein the friction-lock knob is adapted to rotate relative to the channeled platform to selectably clamp the channeled platform between the cover disk and the pivotable base; and
a knob receiver, wherein the friction-lock knob is fixedly attached to the knob receiver, wherein the knob receiver comprises a downwardly-pressing surface adapted to press on an upper surface of the cover disk upon rotation of the friction-lock knob in a first direction.

24. The deflection actuator of claim 18 further comprising:
a second slider trough comprising part of the channeled platform,
a second slider slidably mounted in the second slider trough,
a second cam arm pivotally connected to the pivotable base and adapted to push the second slider in the second slider trough upon pivotable motion of the pivotable base relative to the channeled platform.

25. The deflection actuator of claim 24, further comprising:
a crossmember fixedly attached to the pivotable base; and
a first thumb boss and a second thumb boss, where the first and second thumb bosses are attached to or comprise an integral part of the crossmember.

26. The deflection actuator of claim 18 further comprising a first tension member anchor adapted to selectably anchor a first tension member to the first slider.

27. The deflection actuator of claim 18, wherein the first slider further comprises a slider pushed end, and wherein the first cam arm comprises an arcuate pushing end adapted to press against the slider pushed end.

28. The deflection actuator of claim 18 further comprising (i) a second slider trough formed in the channeled platform, (ii) a second slider slidably mounted in the second slider trough, and (iii) a second cam arm pivotally connected to the pivotable base and adapted to push the second slider in the second slider trough upon pivotable motion of the pivotable base relative to the channeled platform.

29. The deflection actuator of claim 28, wherein the first cam arm comprises a first end that is pivotally mounted to a first pin block on the pivotable base, and wherein the second cam arm comprises a first end that is pivotally mounted to a second pin block on the pivotable base.

30. The deflection actuator of claim 29,
wherein the first cam arm further comprises a second end, wherein a first roller is rotatably mounted to the second end of the first cam arm, and wherein the first roller is adapted to roll in the first trough; and
wherein the second cam arm further comprises a second end, wherein a second roller is rotatably mounted to the second end of the second cam arm, and wherein the second roller is adapted to roll in the second trough.

* * * * *